US011104499B2

(12) United States Patent
Mazzola et al.

(10) Patent No.: US 11,104,499 B2
(45) Date of Patent: Aug. 31, 2021

(54) FLEXIBLE POUCH WITH MICROCAPILLARY DISPENSING SYSTEM

(71) Applicant: Dow Global Technologies LLC, Midland, MI (US)

(72) Inventors: Nicolas C. Mazzola, Jundiai (BR); Wenyi Huang, Midland, MI (US); Laura J. Dietsche, Midland, MI (US); Zhongbi Chen, Midland, MI (US); Bruno R. Pereira, Santana de Parnaiba (BR); Narayan Ramesh, Pearland, TX (US)

(73) Assignee: Dow Global Technologies LLC, Midland, MI (US)

( * ) Notice: Subject to any disclaimer, the term of this patent is extended or adjusted under 35 U.S.C. 154(b) by 384 days.

(21) Appl. No.: 16/310,883

(22) PCT Filed: Jun. 26, 2017

(86) PCT No.: PCT/US2017/039192
§ 371 (c)(1),
(2) Date: Dec. 18, 2018

(87) PCT Pub. No.: WO2018/005319
PCT Pub. Date: Jan. 4, 2018

(65) Prior Publication Data
US 2020/0307885 A1    Oct. 1, 2020

Related U.S. Application Data

(60) Provisional application No. 62/355,565, filed on Jun. 28, 2016.

(51) Int. Cl.
*B65D 75/58* (2006.01)
*B05B 11/04* (2006.01)
(Continued)

(52) U.S. Cl.
CPC ........ *B65D 75/5811* (2013.01); *B05B 11/047* (2013.01); *B65D 35/10* (2013.01);
(Continued)

(58) Field of Classification Search
CPC .... B65D 75/5811; B65D 35/10; B65D 35/36; B65D 75/5822; B65D 75/5866; A01G 25/14; A61M 35/003
See application file for complete search history.

(56) References Cited

U.S. PATENT DOCUMENTS 2,517,027 A * 8/1950 Leopold ............. B65D 47/2031
222/94
3,155,282 A * 11/1964 Leblanc ............. B65D 75/5811
222/107
(Continued)

FOREIGN PATENT DOCUMENTS

| CN | 101486437 A | 7/2009 |
| JP | H1159704 A | 3/1999 |
| KR | 20010070639 A | 7/2001 |

*Primary Examiner* — Vishal Pancholi
(74) *Attorney, Agent, or Firm* — Quarles & Brady LLP

(57) ABSTRACT

The present disclosure provides a flexible pouch. In an embodiment, the flexible pouch includes opposing flexible films. The flexible films define a common peripheral edge. A microcapillary strip is sealed between the opposing flexible films. A first side of the microcapillary strip is located at a first side of the common peripheral edge and a second side of the microcapillary strip located at a second side of the common peripheral edge. A peripheral seal extends along at least a portion of the common peripheral edge. The peripheral seal comprises a sealed microcapillary segment. The peripheral seal forms a closed flexible pouch having a storage compartment. A liquid is present in the storage compartment.

12 Claims, 16 Drawing Sheets

(51) Int. Cl.
   *B65D 35/10*   (2006.01)
   *B65D 35/36*   (2006.01)
   *A01G 25/14*   (2006.01)
   *A61M 35/00*   (2006.01)
   *B65D 85/72*   (2006.01)

(52) U.S. Cl.
   CPC ......... *B65D 35/36* (2013.01); *B65D 75/5822* (2013.01); *B65D 75/5866* (2013.01); *A01G 25/14* (2013.01); *A61M 35/003* (2013.01); *B65D 85/72* (2013.01)

(56) References Cited

U.S. PATENT DOCUMENTS

| | | | |
|---|---|---|---|
| 4,576,316 A * | 3/1986 | Foster | B65D 75/5894 |
| | | | 206/484 |
| 8,002,468 B2 | 8/2011 | Otsuka et al. | |
| 9,061,819 B2 * | 6/2015 | Kane, Jr. | B65D 81/3266 |
| 2003/0123919 A1 * | 7/2003 | Gueret | A45D 34/00 |
| | | | 401/130 |
| 2008/0164288 A1 * | 7/2008 | Singleton | A01C 15/02 |
| | | | 222/465.1 |
| 2009/0011182 A1 * | 1/2009 | Mackley | B29C 48/11 |
| | | | 428/119 |
| 2015/0315345 A1 | 11/2015 | Zalamea et al. | |
| 2016/0016679 A1 | 1/2016 | Pereira et al. | |
| 2017/0183461 A1 | 6/2017 | McKena et al. | |

* cited by examiner

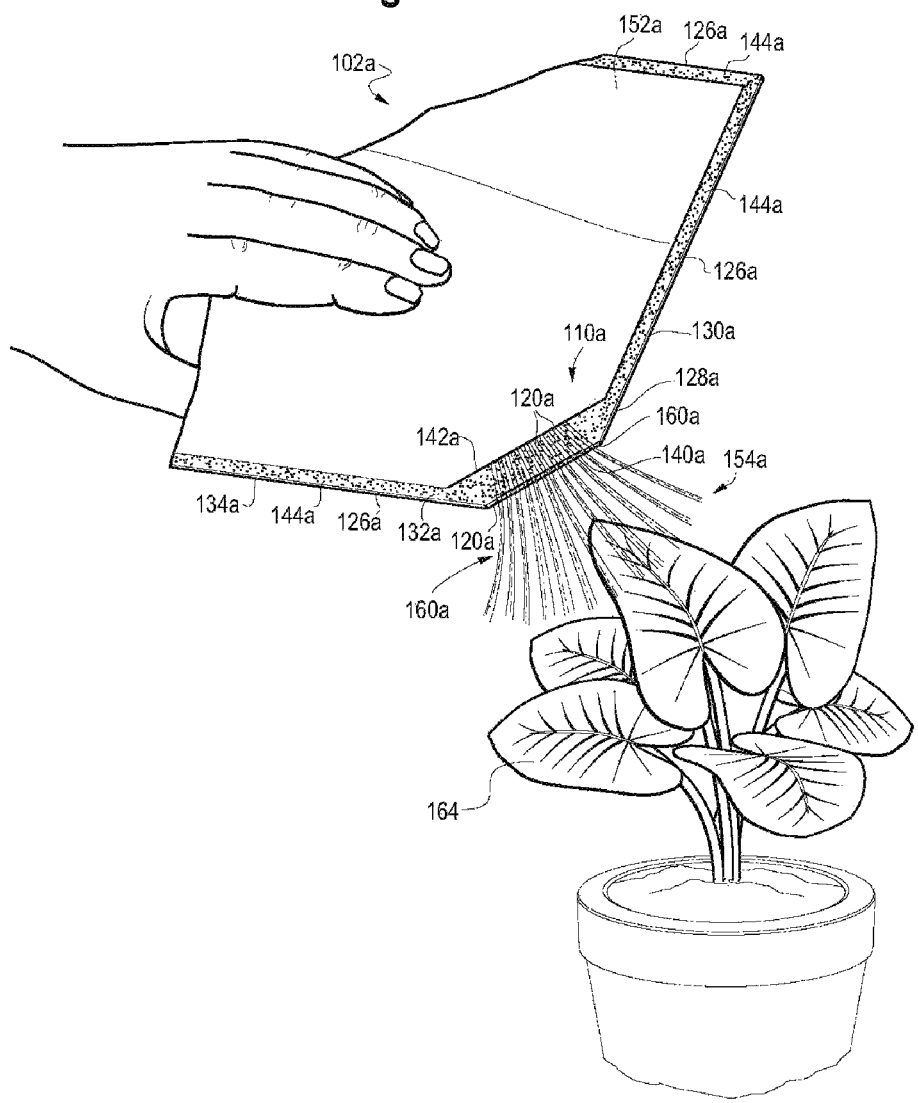

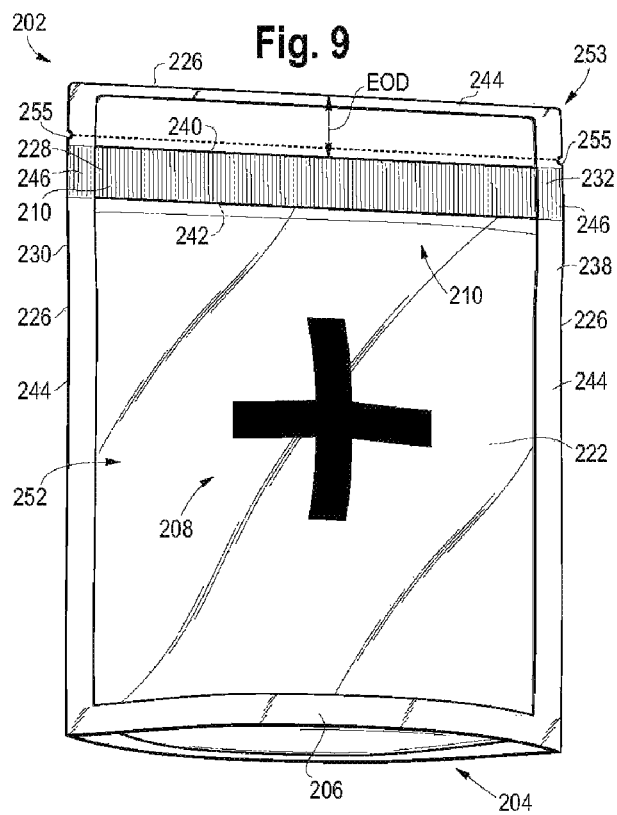
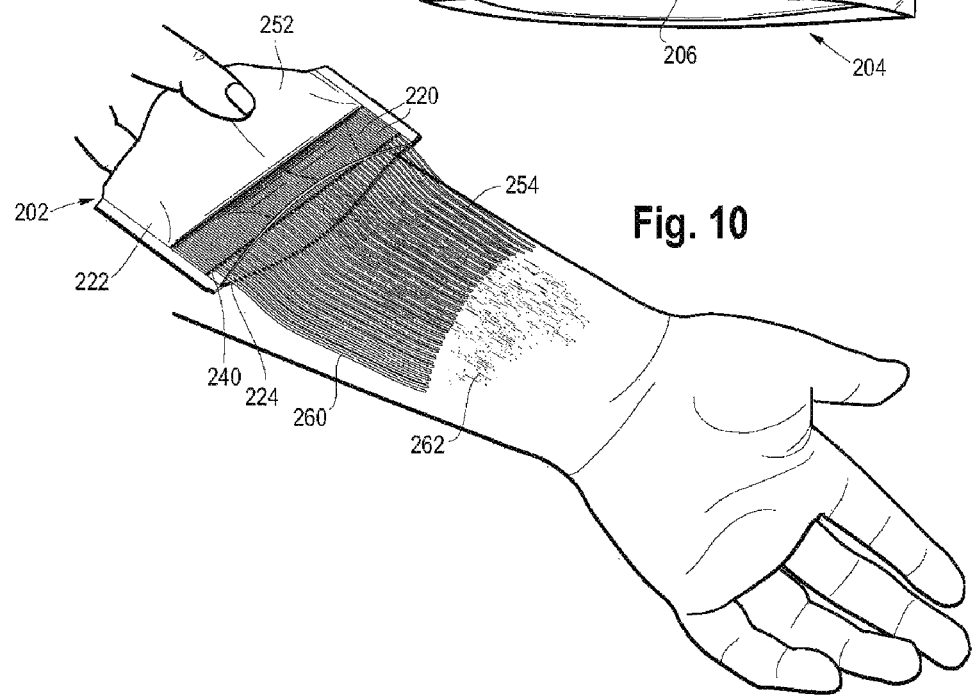

US 11,104,499 B2

FLEXIBLE POUCH WITH MICROCAPILLARY DISPENSING SYSTEM

BACKGROUND

The present disclosure is directed to a flexible pouch with a microcapillary dispensing system.

Flexible pouches are gaining market acceptance versus rigid packaging in many applications. In the food, home care, and personal care segments, flexible pouches offer the advantages of lower weight, efficient use and access to contents, good visual appeal, and better overall sustainability compared to rigid packaging.

Utilization of flexible pouches is still limited due to lack of specific functionalities, such as flow control, for example. Thus, flexible pouches are typically used as refill packages where the flexible pouch is opened and its contents poured into a previously used rigid container having a removable nozzle or spout. The nozzle or spout provides the rigid container with precision flow control.

Attempts for flow control in flexible pouches are achieved in stand-up pouches (SUPS) with the addition of a rigid fitment that is assembled to the SUP flexible structure by a heat-sealing process. These rigid fitments typically have a canoe shaped base that is placed between the films that form the SUP, the films are heat-sealed using a specialized heat seal bar that has the unique shape to accommodate the spout base. The heat sealing process is inefficient as it is slow, requiring specialized tooling. The heat sealing process is prone to significant amount of failures (leaks) due to frequent misalignment of the spout to shaped heat bars resulting in poor contact and sealing between spout and films. The heat sealing process requires careful quality control, thus the high final cost of the fitment in a SUP makes it prohibitive for some low cost applications.

Rigid containers currently dominate the spray segment. Commonplace are rigid containers with specialized spray nozzles or trigger pump sprays for the application of familiar household products such as disinfectants, glass cleansers, and liquid waxes; personal care items such as creams, lotions, and sunscreen; and even food products such as salad dressings and sauces.

Despite the spray control afforded by such packaging systems, rigid containers are disadvantageous because they are heavy, expensive to produce, and the spray component is typically not recyclable.

The art recognizes the need for a flexible pouch that is capable of delivering its content by way of a spray application and without the need for a rigid spray component. A need further exists for a flexible container that is lightweight, recyclable and requires no rigid components.

SUMMARY

The present disclosure provides a flexible pouch capable of delivering a spray—and without any rigid components.

An advantage of the present disclosure is a pillow pouch, a sachet, or a flexible SUP that is capable of delivering a controlled spray of a liquid, without the need for a rigid spray component.

The present disclosure provides a flexible pouch. In an embodiment, the flexible pouch includes opposing flexible films. The flexible films define a common peripheral edge. A microcapillary strip is sealed between the opposing flexible films. A first side of the microcapillary strip is located at a first side of the common peripheral edge and a second side of the microcapillary strip located at a second side of the common peripheral edge. A peripheral seal extends along at least a portion of the common peripheral edge. The peripheral seal comprises a sealed microcapillary segment. The peripheral seal forms a closed flexible pouch having a storage compartment. A liquid is present in the storage compartment.

The present disclosure provides another flexible pouch. In an embodiment, the flexible pouch has opposing flexible films. The flexible films define a common peripheral edge. A microcapillary strip is located at an edge offset distance between the opposing flexible films. The microcapillary strip is sealed between the opposing flexible films. A first side of the microcapillary strip is located at a first side of the common peripheral edge and a second side of the microcapillary strip is located at a second side of the common peripheral edge. A peripheral seal extends along at least a portion of the common peripheral edge. The peripheral edge comprises a sealed microcapillary segment. The peripheral seal forms a closed flexible pouch having a storage compartment and a pocket. A liquid is present in the storage compartment.

The present disclosure provides another flexible pouch. In an embodiment, the flexible pouch includes opposing flexible films. The flexible films define a common peripheral edge. A microcapillary strip is sealed between the opposing flexible films. The microcapillary strip comprises opposing sides and opposing edges. A peripheral seal extends along at least a portion of the common peripheral edge. The peripheral seal comprises (i) a side seal extending along each side of the microcapillary strip, and (ii) an edge seal extending along an outer edge of the microcapillary strip. The peripheral seal forms a closed flexible pouch having a storage compartment.

BRIEF DESCRIPTION OF THE DRAWINGS

FIG. 8A is a perspective view of microcapillary dispensing with non-parallel channels in accordance with an embodiment of the present disclosure.

FIG. 9 is a perspective view of a flexible pouch with a microcapillary dispensing system in accordance with another embodiment of the present disclosure.

FIG. 10 is a perspective view of microcapillary dispensing in accordance with another embodiment of the present disclosure.

DEFINITIONS

Figure 1:
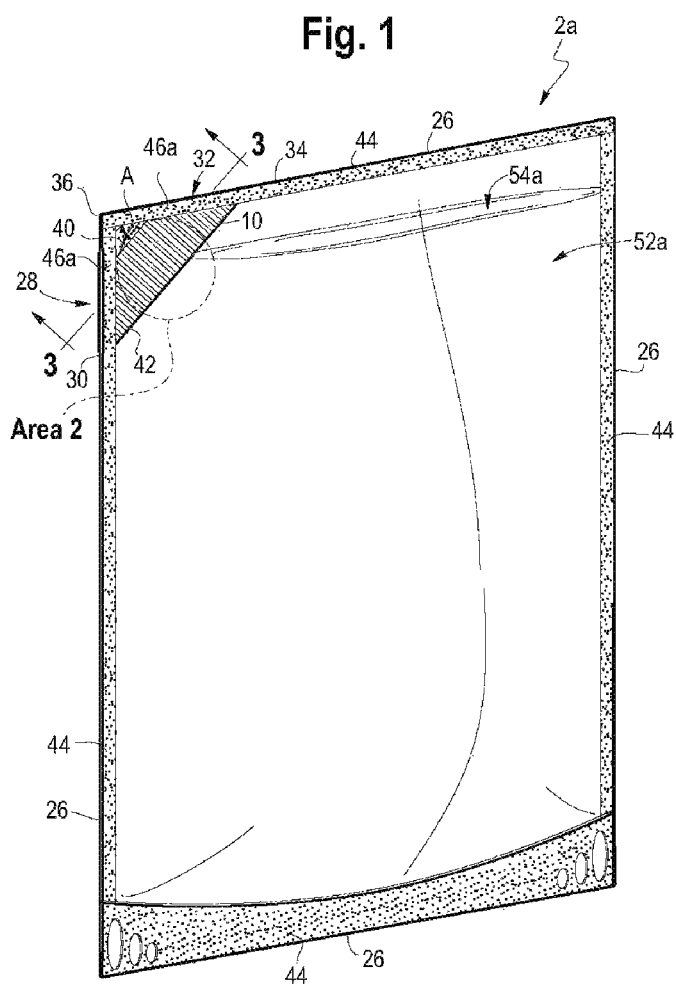
FIG. 1 is perspective view of a flexible pouch with a microcapillary dispensing system in accordance with an embodiment of the present disclosure.

All references to the Periodic Table of the Elements herein shall refer to the Periodic Table of the Elements, published and copyrighted by CRC Press, Inc., 2003. Also, any references to a Group or Groups shall be to the Groups or Groups reflected in this Periodic Table of the Elements using the IUPAC system for numbering groups. Unless stated to the contrary, implicit from the context, or customary in the art, all parts and percents are based on weight. For purposes of United States patent practice, the contents of any patent, patent application, or publication referenced herein are hereby incorporated by reference in their entirety (or the equivalent US version thereof is so incorporated by reference), especially with respect to the disclosure of synthetic techniques, definitions (to the extent not inconsistent with any definitions provided herein) and general knowledge in the art.

The numerical ranges disclosed herein include all values from, and including, the lower value and the upper value. For ranges containing explicit values (e.g., 1, or 2, or 3 to 5, or 6, or 7) any subrange between any two explicit values is included (e.g., 1 to 2; 2 to 6; 5 to 7; 3 to 7; 5 to 6; etc.).

Unless stated to the contrary, implicit from the context, or customary in the art, all parts and percents are based on weight, and all test methods are current as of the filing date of this disclosure.

The term "composition," as used herein, refers to a mixture of materials which comprise the composition, as well as reaction products and decomposition products formed from the materials of the composition.

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed.

The term "contact angle" is the angle formed by the intersection of the liquid-solid interface and liquid-vapor interface when a liquid drop is resting on a flat horizontal solid surface, the flat horizontal solid surface composed of the matrix material. The contact angle is geometrically acquired by applying a tangent line from the contact point along the liquid-vapor interface in the droplet profile, with the angle passing through the liquid phase. A contact angle less than 90° indicates that wetting of the surface is favorable, and the liquid will spread over a large area on the surface. A contact angle greater than or equal to 90° indicates that wetting of the surface is unfavorable so the liquid will minimize its contact with the surface of the matrix material to form a compact liquid droplet. Contact angle is measured in accordance with ASTM D 5946.

Density is measured in accordance with ASTM D 792 with results reported in grams (g) per cubic centimeter (cc), or g/cc.

An "ethylene-based polymer," as used herein, is a polymer that contains more than 50 mole percent polymerized ethylene monomer (based on the total amount of polymerizable monomers) and, optionally, may contain at least one comonomer.

Melt flow rate (MFR) is measured in accordance with ASTM D 1238, Condition 280° C./2.16 kg (g/10 minutes).

Melt index (MI) is measured in accordance with ASTM D 1238, Condition 190° C./2.16 kg (g/10 minutes).

Shore A hardness is measured in accordance with ASTM D 2240.

Tm or "melting point," as used herein, (also referred to as a melting peak in reference to the shape of the plotted DSC curve) is typically measured by the DSC (Differential Scanning calorimetry) technique for measuring the melting points or peaks of polyolefins as described in U.S. Pat. No. 5,783,638. It should be noted that many blends comprising two or more polyolefins will have more than one melting point or peak, many individual polyolefins will comprise only one melting point or peak.

An "olefin-based polymer," as used herein, is a polymer that contains more than 50 mole percent polymerized olefin monomer (based on total amount of polymerizable monomers), and optionally, may contain at least one comonomer. Nonlimiting examples of olefin-based polymer include ethylene-based polymer and propylene-based polymer.

A "polymer" is a compound prepared by polymerizing monomers, whether of the same or a different type, that in polymerized form provide the multiple and/or repeating "units" or "mer units" that make up a polymer. The generic term polymer thus embraces the term homopolymer, usually employed to refer to polymers prepared from only one type of monomer, and the term copolymer, usually employed to refer to polymers prepared from at least two types of monomers. It also embraces all forms of copolymer, e.g., random, block, etc. The terms "ethylene/α-olefin polymer" and "propylene/α-olefin polymer" are indicative of copolymer as described above prepared from polymerizing ethylene or propylene respectively and one or more additional, polymerizable α-olefin monomer. It is noted that although a polymer is often referred to as being "made of" one or more specified monomers, "based on" a specified monomer or monomer type, "containing" a specified monomer content, or the like, in this context the term "monomer" is understood to be referring to the polymerized remnant of the specified monomer and not to the unpolymerized species. In general, polymers herein are referred to has being based on "units" that are the polymerized form of a corresponding monomer.

A "propylene-based polymer" is a polymer that contains more than 50 mole percent polymerized propylene monomer (based on the total amount of polymerizable monomers) and, optionally, may contain at least one comonomer.

Surface tension. (1) Material surface tension. The term "material surface tension," or "M-surface tension" (also known as the "critical surface tension") for a solid is the surface energy that a liquid must have for the contact angle with the solid to be exactly zero and hence spontaneously and completely wet out the surface. The M-surface tension is measured in accordance with ASTM D 2578 and reported in dynes per centimeter, or dyn/cm. (2) Liquid surface tension. The term "liquid surface tension" or "L-surface tension" is the attractive force exerted upon the surface molecules of a liquid by the molecules beneath that tends to draw the surface molecules into the bulk of the liquid and makes the liquid assume the shape having the least surface area. The L-surface tension is measured in accordance with ASTM D 2578 and is reported in dyn/cm.

DETAILED DESCRIPTION

The present disclosure provides a flexible pouch. In an embodiment, the flexible pouch includes opposing flexible films. The opposing flexible films define a common peripheral edge. A microcapillary strip is sealed between the opposing flexible films. A first side of the microcapillary strip is located at a first side of the common peripheral edge and a second side of the microcapillary strip is located at a second side of the common peripheral edge. A peripheral seal extends along at least a portion of the common peripheral edge. The peripheral seal includes a sealed microcapillary segment.

1. Microcapillary Strip

Figure 2:
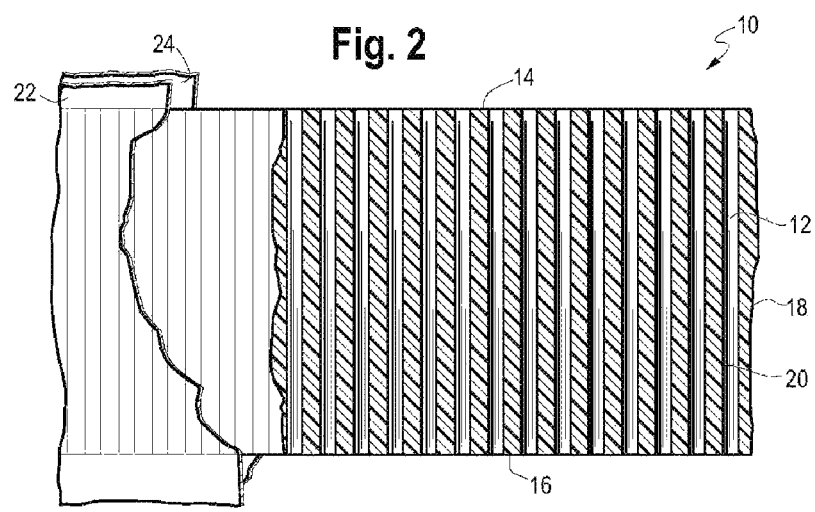
FIG. 2 is a cut-away view of area 2 of FIG. 1.
Figure 3:
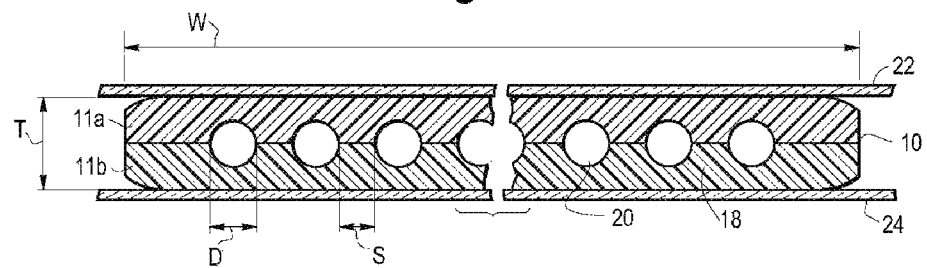
FIG. 3 is a cross sectional view of the microcapillary strip taken along line 3-3 of FIG. 1.
Figure 3A:
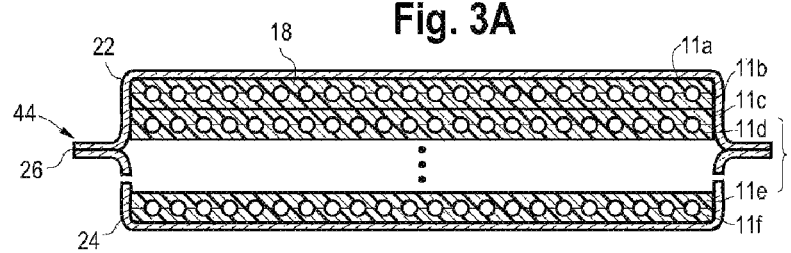
FIG. 3A is a sectional view of a microcapillary strip in accordance with an embodiment of the present disclosure.

FIGS. 1-3A depict various views of a microcapillary strip 10 (or strip 10). The microcapillary strip 10 is composed of multiple layers (11a, 11b) of a polymeric material. While only two layers (11a, 11b) are depicted in FIG. 3, the microcapillary strip 10 may include one, or three, or four, or five, or six, or more layers 11a-11b, as shown in FIG. 3A.

As shown in FIGS. 2 and 3, the microcapillary strip 10 has void volumes 12 and a first end 14 and a second end 16. The microcapillary strip 10 is composed of a matrix 18, which is a polymeric material. The matrix 18 may comprise reciprocal layers (such as layers 11a, 11b). Alternatively, matrix 18 may be an integral and uniform polymeric material made by way of in situ microcapillary strip production as disclosed in WO 2017/003865, published 5 Jan. 2017, the entire content of which is incorporated by reference herein.

One or more channels 20 are disposed in the matrix 18. The channels 20 are arranged alongside and extend from the first end 14 to the second end 16 of the microcapillary strip 10. The channels 20 are positioned between the layers 11a, 11b. The number of channels 20 may be varied as desired. Each channel 20 has a cross-sectional shape. Nonlimiting examples of suitable cross-sectional shapes for the channels include oval, ovoid, circle, curvilinear, triangle, square, rectangle, star, diamond, and combinations thereof.

It is desired that the polymeric material has low shrink and release properties. In addition, it is recognized that a factor in the retention and/or ease of discharge of the liquid product stored in the flexible container is the surface tension between (i) the channel (or capillary) surfaces and (ii) the liquid content of the flexible container. Applicant discovered that altering the surface tension, or otherwise optimizing surface tension, for a particular use may improve performance of the flexible pouch. Nonlimiting examples of suitable methods to alter surface tension include material selection of the layers 11a, 11b and/or matrix 18; addition of surface coatings to the layers 11a, 11b and/or matrix 18; surface treatment of the layers 11a, 11b and/or matrix 18 and/or the resultant channels 20 (i.e., corona treatment); and addition of additives either to the layers 11a, 11b and/or matrix 18, or to the liquid to be stored in the flexible container.

The channels 20 have a diameter, D, as shown in FIG. 3. The term "diameter," as used herein, is the longest axis of the channel 20, from a cross-sectional view. In an embodiment, the diameter, D, is from 50 μm, or 100 μm, or 150 μm, or 200 μm to 250 μm, or 300 μm, or 350 μm, or 400 μm, or 500 μm, or 600 μm, or 700 μm, or 800 μm, or 900 μm, or 1000 μm.

In an embodiment, the diameter, D, is from 300 μm, or 400 μm, or 500 μm to 600 μm, or 700 μm, or 800 μm, or 900 μm or 1000 μm.

The channels 20 may or may not be parallel with respect to each other. The term "parallel," as used herein, means extending in the same direction and never intersecting.

In an embodiment, the channels 20 are parallel.

In an embodiment, the channels 20 are not parallel, or are non-parallel.

A spacing, S, of matrix 18 (polymeric material) is present between the channels 20. In an embodiment, the spacing, S, is from 1 micrometer (μm), or 5 μm, or 10 μm, or 25 μm, or 50 μm, or 100 μm, or 150 μm, or 200 μm to 250 μm, or 300 μm, or 350 μm, or 400 μm, or 500 μm, or 1000 μm, or 2000 μm or 3000 μm.

The microcapillary strip 10 has a thickness, T, and a width, W, as shown in FIG. 3. In an embodiment, the thickness, T, is from 10 μm, or 20 μm, or 30, or 40 μm, or 50 μm, or 60 μm, or 70 μm, or 80 μm, or 90 μm, or 100 μm to 200 μm, or 500 μm, or 1000 μm, or 1500 μm, or 2000 μm.

In an embodiment, the short axis of microcapillary is from 20%, or 30%, or 40%, or 50% to 60%, or 70%, or 80% of the thickness, T. Short axis is the shortest axis of the channel (20) from the cross section point of view. Shortest axis is typically the "height" of the channel considering the microcapillary strip in a horizontal position.

In an embodiment, the microcapillary strip 10 has a thickness, T, from 50 μm, or 60 μm, or 70 μm, or 80 μm, or 90 μm, or 100 μm to 200 μm, or 500 μm, or 1000 μm, or 1500 μm, or 2000 μm. In a further embodiment, the microcapillary strip 10 has a thickness, T, from 600 μm to 1000 μm.

In an embodiment, the microcapillary strip 10 has a width, W, from 0.5 centimeter (cm), or 1.0 cm, or 1.5 cm, or 2.0 cm, or 2.5 cm, or 3.0 cm, or 5.0 cm to 8.0 cm, or 10.0 cm, or 20.0 cm, or 30.0 cm, or 40.0 cm, or 50.0 cm, or 60.0 cm, or 70.0 cm, or 80.0 cm, or 90.0 cm, or 100.0 cm.

In an embodiment, the microcapillary strip 10 has a width, W, from 0.5 cm, or 1.0 cm, or 2.0 cm to 2.5 cm, or 3.0 cm, or 4.0 cm, or 5.0 cm.

In an embodiment, the microcapillary strip 10 has a diameter, D, from 300 μm to 1000 μm, a spacing, S, from 300 μm to 2000 μm, a thickness, T, from 50 μm to 2000 μm, and a width, W, from 1.0 cm to 4.0 cm.

The microcapillary strip 10 may comprise at least 10 percent by volume of the matrix 18, based on the total volume of the microcapillary strip 10; for example, the microcapillary strip 10 may comprise from 90 to 10 percent by volume of the matrix 18, based on the total volume of the microcapillary strip 10; or in the alternative, from 80 to 20 percent by volume of the matrix 18, based on the total volume of the microcapillary film 10; or in the alternative, from 80 to 30 percent by volume of the matrix 18, based on the total volume of the microcapillary strip 10, or in the alternative, from 80 to 50 percent by volume of the matrix (18), based on the total volume of the microcapillary strip 10.

The microcapillary strip 10 may comprise from 10 to 90 percent by volume of voidage, based on the total volume of the microcapillary strip 10; for example, the microcapillary strip 10 may comprise from 20 to 80 percent by volume of voidage, based on the total volume of the microcapillary strip 10; or in the alternative, from 20 to 70 percent by volume of voidage, based on the total volume of the microcapillary strip 10; or in the alternative, from 20 to 50 percent by volume of voidage, based on the total volume of the microcapillary strip 10.

The matrix 18 is composed of one or more polymeric materials. Nonlimiting examples of suitable polymeric materials for the polymeric strips 4a, 4b include ethylene/$C_3$-$C_{10}$ α-olefin copolymers linear or branched; ethylene/$C_4$-$C_{10}$ α-olefin copolymers linear or branched; propylene-based polymer (including plastomer and elastomer, random propylene copolymer, propylene homopolymer, and propylene impact copolymer); ethylene-based polymer (including plastomer and elastomer, high density polyethylene ("HDPE"), low density polyethylene ("LDPE"), linear low density polyethylene ("LLDPE"), medium density polyethylene ("MDPE")); ethylene-acrylic acid or ethylene-methacrylic acid and their ionomers with zinc, sodium, lithium, potassium, magnesium salts; ethylene vinyl acetate copolymers; and blends thereof.

In an embodiment, the matrix 18 is composed of one or more of the following polymers: enhanced polyethylene resin ELITE™ 5100 G with a density of 0.92 g/cc by ASTM D792, a Melt Index of 0.85 g/10 min@190° C., 2.16 kg by ASTM D1238, and melt temperature of 123° C.; low density polyethylene resin DOW™ LDPE 5011 with a density of 0.922 g/cc by ASTM D792, a Melt Index of 1.9 g/10 min@190° C., 2.16 kg, and a melting temperature of 111° C.; high density polyethylene resin UNIVAL™ DMDA-6400 NT7 with a density of 0.961 g/cc by ASTM D792, a Melt Index of 0.8 g/10 min@190° C., 2.16 kg, and a melting temperature of 111° C.; polypropylene Braskem PP H314-02Z with a density of 0.901 g/cc by ASTM D792, a Melt Index of 2.0 g/10 min@230° C., 2.16 kg, and a melting temperature of 163° C., ethylene/$C_4$-$C_{12}$ α-olefin multi-block copolymer such INFUSE™ 9817, INFUSE™ 9500, INFUSE™ 9507, INFUSE™ 9107, INFUSE™ 9100 available from The Dow Chemical Company.

2. Flexible Film

The present flexible pouch includes opposing flexible films. In an embodiment, the flexible pouch includes two opposing flexible films. Each flexible film can be a monolayer film or a multilayer film. The two opposing films may be components of a single (folded) sheet/web, or may be separate and distinct films. The composition and structure of each flexible film can be the same or can be different.

In an embodiment, the two opposing flexible films are components of the same sheet or film, wherein the sheet is folded upon itself to form the two opposing films. The three unconnected edges can then be sealed, or heat sealed, after the microcapillary strip is placed between the folded-over films.

In an embodiment, each flexible film is a separate film and is a flexible multilayer film having at least one, or at least two, or at least three layers. The flexible multilayer film is resilient, flexible, deformable, and pliable. The structure and composition for each of the two flexible multilayer films may be the same or different. For example, each of the two flexible films can be made from a separate web, each web having a unique structure and/or unique composition, finish, or print. Alternatively, each of two flexible films can be the same structure and the same composition, or from a single web.

In an embodiment, flexible film 22 and flexible film 24 each is a flexible multilayer film having the same structure and the same composition from a single web.

Each flexible multilayer film 22, 24 may be (i) a coextruded multilayer structure or (ii) a laminate, or (iii) a combination of (i) and (ii). In an embodiment, each flexible multilayer film 22, 24 has at least three layers: a seal layer, an outer layer, and a tie layer between. The tie layer adjoins the seal layer to the outer layer. The flexible multilayer film may include one or more optional inner layers disposed between the seal layer and the outer layer.

In an embodiment, the flexible multilayer film is a coextruded film having at least two, or three, or four, or five, or six, or seven to eight, or nine, or ten, or eleven, or more layers. Some methods, for example, used to construct films are by cast co-extrusion or blown co-extrusion methods, adhesive lamination, extrusion lamination, thermal lamination, and coatings such as vapor deposition. Combinations of these methods are also possible. Film layers can comprise, in addition to the polymeric materials, additives such as stabilizers, slip additives, antiblocking additives, process aids, clarifiers, nucleators, pigments or colorants, fillers and reinforcing agents, and the like as commonly used in the packaging industry. It is particularly useful to choose additives and polymeric materials that have suitable organoleptic and or optical properties.

The flexible multilayer film is composed of one or more polymeric materials. Nonlimiting examples of suitable polymeric materials for the seal layer include olefin-based polymer including any ethylene/$C_3$-$C_{10}$ α-olefin copolymers linear or branched; ethylene/$C_4$-$C_{10}$ α-olefin copolymers linear or branched; propylene-based polymer (including plastomer and elastomer, and random propylene copolymer); ethylene-based polymer (including plastomer and elastomer, high density polyethylene ("HDPE"), low density polyethylene ("LDPE"), linear low density polyethylene ("LLDPE"), medium density polyethylene ("MDPE")); ethylene-acrylic acid; ethylene vinyl acetate; or ethylene-methacrylic acid and their ionomers with zinc, sodium, lithium, potassium, magnesium salts; ethylene vinyl acetate copolymers; and blends thereof.

Nonlimiting examples of suitable polymeric material for the outer layer include those used to make biaxially or monoaxially oriented films for lamination as well as coextruded films. Some nonlimiting polymeric material examples are biaxially oriented polyethylene terephthalate (OPET), monoaxially oriented nylon (MON), biaxially oriented nylon (BON), and biaxially oriented polypropylene (BOPP). Other polymeric materials useful in constructing film layers for structural benefit are polypropylenes (such as propylene homopolymer, random propylene copolymer, propylene impact copolymer, thermoplastic polypropylene (TPO) and the like, propylene-based plastomers (e.g., VERSIFY™ or VISTAMAX™)), polyamides (such as Nylon 6, Nylon 6,6, Nylon 6,66, Nylon 6,12, Nylon 12, etc.), polyethylene norbornene, cyclic olefin copolymers, polyacrylonitrile, polyesters, copolyesters (such as polyethylene terephthalate-glycol (PETG)), cellulose esters, polyethylene and copolymers of ethylene (e.g., LLDPE based on ethylene octene copolymer such as DOWLEX™, blends thereof, and multilayer combinations thereof.

Nonlimiting examples of suitable polymeric materials for tie layer include functionalized ethylene-based polymers such as ethylene-vinyl acetate ("EVA") copolymer, polymers with maleic anhydride-grafted to polyolefins such as any polyethylene, ethylene-copolymers, or polypropylene, and ethylene acrylate copolymers such as ethylene methyl acrylate ("EMA") copolymer, glycidyl containing ethylene copolymers, propylene and ethylene based olefin block copolymers such as INFUSE™ (Olefin Block Copolymers available from the Dow Chemical Company) and INTUNE™ (PP-based Olefin Block Copolymers available from The Dow Chemical Company), and blends thereof.

The flexible multilayer film may include additional layers which may contribute to the structural integrity or provide specific properties. The additional layers may be added by direct means or by using appropriate tie layers to the adjacent polymer layers. Polymers which may provide additional performance benefits such as stiffness, toughness or opacity, as well polymers which may offer gas barrier properties or chemical resistance can be added to the structure.

Nonlimiting examples of suitable material for the optional barrier layer include copolymers of vinylidene chloride and methyl acrylate, methyl methacrylate or vinyl chloride (e.g., SARAN resins available from The Dow Chemical Company); vinylethylene vinyl alcohol (EVOH) copolymer, metal foil (such as aluminum foil). Alternatively, modified polymeric films such as vapor deposited aluminum or silicon oxide on such films as BON, OPET, or oriented polypropylene (OPP), can be used to obtain barrier properties when used in laminate multilayer film.

In an embodiment, the flexible multilayer film includes a seal layer selected from LLDPE (sold under the trade name DOWLEX™ (The Dow Chemical Company)), single-site LLDPE substantially linear, or linear ethylene alpha-olefin copolymers, including polymers sold under the trade name AFFINITY™ or ELITE™ (The Dow Chemical Company) for example, propylene-based plastomers or elastomers such as VERSIFY™ (The Dow Chemical Company), and blends thereof. An optional tie layer is selected from either ethylene-based olefin block copolymer INFUSE™ Olefin Block Copolymer (available from The Dow Chemical Company) or propylene-based olefin block copolymer such as INTUNE™ (available from The Dow Chemical Company), ethylene-acrylic acid such as PRIMACOR™, ethylene vinyl acetate; or ethylene-methacrylic acid and their ionomers with zinc, sodium, lithium, potassium, magnesium salts, such as AMPLIFY 10 and blends thereof. The outer layer includes greater than 50 wt % of resin(s) having a melting point, Tm, that is from 25° C. to 30° C., or 40° C. or higher than the melting point of the polymer in the seal layer wherein the outer layer polymer is comprised of resins such as DOWLEX LLDPE, ELITE enhanced polyethylene resin, MDPE, HDPE, LDPE or a propylene-based polymer such as VERSIFY or VISTAMAX, propylene homopolymer, propylene impact copolymer or TPO.

In an embodiment, the flexible multilayer film is co-extruded.

In an embodiment, flexible multilayer film includes a seal layer selected from LLDPE (sold under the trade name DOWLEX™ (The Dow Chemical Company)), single-site LLDPE (substantially linear, or linear, olefin polymers, including polymers sold under the trade name AFFINITY™ or ELITE™ (The Dow Chemical Company) for example, propylene-based plastomers or elastomers such as VERSIFY™ (The Dow Chemical Company), and blends thereof. The flexible multilayer film also includes an outer layer that is a polyamide.

In an embodiment, the flexible multilayer film is a coextruded film and includes:
(i) a seal layer composed of an olefin-based polymer having a first melt temperature less than 105° C., (Tm1); and
(ii) an outer layer composed of a polymeric material having a second melt temperature, (Tm2),
wherein Tm2−Tm1>40° C.

The term "Tm2−Tm1" is the difference between the melt temperature of the polymer in the outer layer (Tm2) and the melt temperature of the polymer in the seal layer (Tm1), and is also referred to as "ΔTm." In an embodiment, the ΔTm is from 41° C., or 50° C., or 75° C., or 100° C. to 125° C., or 150° C., or 175° C., or 200° C.

In an embodiment, the flexible multilayer film is a coextruded film, the seal layer is composed of an ethylene-based polymer, such as a linear or a substantially linear polymer, or a single-site catalyzed linear or substantially linear polymer of ethylene and an alpha-olefin monomer such as 1-butene, 1-hexene or 1-octene, having a Tm from 55° C. to 115° C. and a density from 0.865 to 0.925 g/cc, or from 0.875 to 0.910 g/cc, or from 0.888 to 0.900 g/cc and the outer layer is composed of a polyamide having a Tm from 170° C. to 270° C.

In an embodiment, the flexible multilayer film is a coextruded and/or laminated film having at least five layers, the coextruded film having a seal layer composed of an ethylene-based polymer, such as a linear or substantially linear polymer, or a single-site catalyzed linear or substantially linear polymer of ethylene and an alpha-olefin comonomer such as 1-butene, 1-hexene or 1-octene, the ethylene-based polymer having a Tm from 55° C. to 115° C. and a density from 0.865 to 0.925 g/cc, or from 0.875 to 0.910 g/cc, or from 0.888 to 0.900 g/cc and an outermost layer composed of a material selected from LLDPE, OPET, OPP (oriented polypropylene), BOPP, polyamide, and combinations thereof.

In an embodiment, the flexible multilayer film is a coextruded and/or laminated film having at least seven layers. The seal layer is composed of an ethylene-based polymer, such as a linear or substantially linear polymer, or a single-site catalyzed linear or substantially linear polymer of ethylene and an alpha-olefin comonomer such as 1-butene, 1-hexene or 1-octene, the ethylene-based polymer having a Tm from 55° C. to 115° C. and density from 0.865 to 0.925 g/cc, or from 0.875 to 0.910 g/cc, or from 0.888 to 0.900 g/cc. The outer layer is composed of a material selected from LLDPE, OPET, OPP (oriented polypropylene), BOPP, polyamide, and combinations thereof.

In an embodiment, the flexible multilayer film is a coextruded (or laminated) five layer film, or a coextruded (or laminated) seven layer film having at least two layers containing an ethylene-based polymer. The ethylene-based polymer may be the same or different in each layer.

In an embodiment, the flexible multilayer film is a coextruded (or laminated) five layer film, or a coextruded (or laminated) seven layer film having all layers containing polyolefin. The polyolefins may be the same or different in each layer. In such a case the entire package created with microcapillary strip included contains polyolefin.

In an embodiment, the flexible multilayer film is a coextruded (or laminated) five layer film, or a coextruded (or laminated) seven layer film having all layers containing an ethylene-based polymer. The ethylene-based polymer may be the same or different in each layer. In such a case the entire package created with microcapillary strip included contains polyethylene.

In an embodiment, the flexible multilayer film includes a seal layer composed of an ethylene-based polymer, or a linear or substantially linear polymer, or a single-site catalyzed linear or substantially linear polymer of ethylene and an alpha-olefin monomer such as 1-butene, 1-hexene or 1-octene, having a heat seal initiation temperature (HSIT) from 65° C. to less than 125° C. Applicant discovered that the seal layer with an ethylene-based polymer with a HSIT from 65° C. to less than 125° C. advantageously enables the formation of secure seals and secure sealed edges around the complex perimeter of the flexible container. The ethylene-based polymer with HSIT from 65° C. to 125° C. enables lower heat sealing pressure/temperature during container fabrication. Lower heat seal pressure/temperature results in lower stress at the fold points of the gusset, and lower stress at the union of the films in the top segment and in the bottom segment. This improves film integrity by reducing wrinkling during the container fabrication. Reducing stresses at the folds and seams improves the finished container mechanical performance. The low HSIT ethylene-based polymer seals at a temperature below what would cause the microcapillary strip dimensional stability to be compromised.

In an embodiment, the seal layer of the flexible multilayer film and the microcapillary strip are composed of the same material, such as an ethylene-based polymer for example.

In an embodiment, the flexible multilayer film is a coextruded and/or laminated five layer, or a coextruded (or laminated) seven layer film having at least one layer containing a material selected from LLDPE, OPET, OPP (oriented polypropylene), BOPP, and polyamide.

In an embodiment, the flexible multilayer film is a coextruded and/or laminated five layer, or a coextruded (or laminated) seven layer film having at least one layer containing OPET or OPP.

In an embodiment, the flexible multilayer film is a coextruded (or laminated) five layer, or a coextruded (or laminated) seven layer film having at least one layer containing polyamide.

In an embodiment, the flexible multilayer film is a seven-layer coextruded (or laminated) film with a seal layer composed of an ethylene-based polymer, or a linear or substantially linear polymer, or a single-site catalyzed linear or substantially linear polymer of ethylene and an alpha-olefin monomer such as 1-butene, 1-hexene or 1-octene, having a Tm from 90° C. to 106° C. The outer layer is a polyamide having a Tm from 170° C. to 270° C. The film has a $\Delta$Tm from 40° C. to 200° C. The film has an inner layer (first inner layer) composed of a second ethylene-based polymer, different than the ethylene-based polymer in the seal layer. The film has an inner layer (second inner layer) composed of a polyamide the same or different to the polyamide in the outer layer. The seven layer film has a thickness from 100 micrometers to 250 micrometers.

In an embodiment, flexible films 22, 24 each has a thickness from 50 micrometers ($\mu$m), or 75 $\mu$m, or 100 $\mu$m, or 150 $\mu$m, or 200 $\mu$m to 250 $\mu$m, or 300 $\mu$m, or 350 $\mu$m, or 400 $\mu$m.

3. Common Peripheral Edge

The opposing flexible films 22 and 24 are superimposed on each other and form a common peripheral edge 26 as shown in FIGS. 1, 4-13. The common peripheral edge 26 defines a shape. The shape can be a polygon (such as triangle, square, rectangle, diamond, pentagon, hexagon, heptagon, octagon, etc.), or an ellipse (such as an ovoid, an oval, or a circle).

The microcapillary strip 10 is sealed between the opposing flexible films 22, 24 and forms a hermetic seal. The seal is formed by way of ultrasonic seal, heat seal, and combinations thereof. In an embodiment, the microcapillary strip 10 is sealed between the opposing flexible films 22, 24 by way of a heat sealing procedure. The term "heat sealing," as used herein, is the act of placing two or more films of polymeric material between opposing heat seal bars, the heat seal bars moved toward each other, sandwiching the films, to apply heat and pressure to the films such that opposing interior surfaces (seal layers) of the films contact, melt, and form a heat seal, or weld, to attach the films to each other. Heat sealing includes suitable structure and mechanism to move the seal bars toward and away from each other in order to perform the heat sealing procedure.

In an embodiment, the seal between the microcapillary strip 10 and the flexible films 22, 24 occurs at a first seal condition. The first seal condition is sufficient: (i) to fuse polymeric material of matrix 18 to the flexible films and (ii) form a hermetic seal between the microcapillary strip 10 and flexible films 22 and 24.

In an embodiment, the first heat seal condition includes a heat seal temperature that (1) is less than the melting temperature, Tm, of the polymeric material for the matrix 18 and (2) is greater than the heat seal initiation temperature seal layer for flexible films 22, 24.

A first side of the microcapillary strip is located at a first side of the common peripheral edge and a second side of the microcapillary strip is located at a second side of the common peripheral edge. In an embodiment, a first side 28 of the microcapillary strip 10 is located at a first side 30 of the common peripheral edge 26 for flexible pouch 2a, shown in FIG. 1. A second side 32 of the microcapillary strip 10 is located at a second side 34 of the common peripheral edge 26. As shown in FIG. 1, the second side 34 of the 4-sided polygon intersects the first side 30 of the 4-sided polygon, the intersection being corner 36 shown in FIG. 1. The microcapillary strip 10 has an outer edge 40 (corresponding to first end 14) and an inner edge 42 (corresponding to second end 16). In an embodiment, the outer edge 40 forms angle A at the corner 36, as shown in FIG. 1. In a further embodiment, angle A is 45°.

A peripheral seal 44 extends along at least a portion of the common peripheral edge 26. The peripheral seal 44 includes a sealed microcapillary segment 46. The peripheral seal 44 can be a heat seal, an ultrasonic seal, an adhesive seal, and combinations thereof. In an embodiment, the peripheral seal is a heat seal produced under a second seal condition. The second seal condition includes (1) a heat seal temperature that is greater than or equal to the Tm of the polymeric material of matrix 18 and (2) a seal pressure that collapses or otherwise crushes a portion of the channels 20 of the microcapillary strip 10.

In an embodiment, the second sealing is a heat sealing procedure and includes sealing, or otherwise forming, a peripheral seal 44 along a portion of the peripheral edge 26. The resultant peripheral seal 44 includes a sealed microcapillary segment either 46a (FIGS. 4-5), or sealed microcapillary segment 46b (FIG. 5A).

Figure 5:
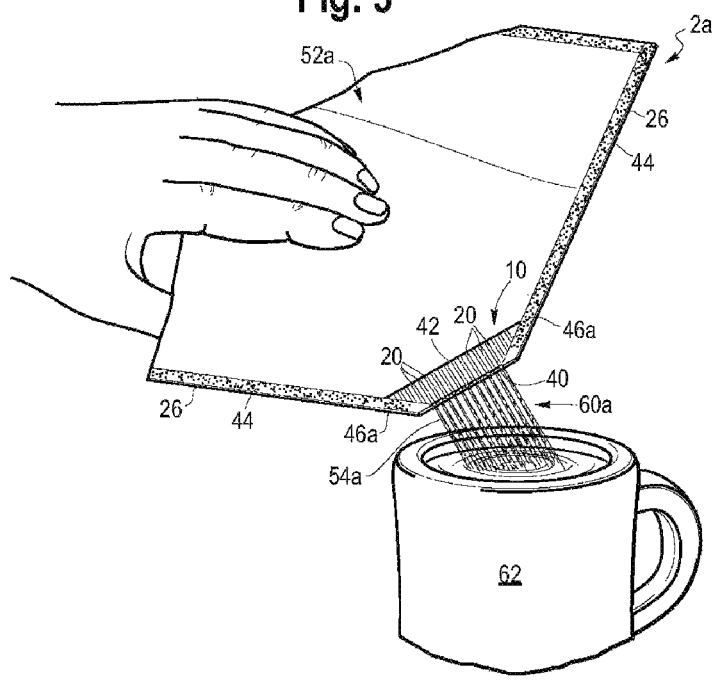
FIG. 5 a perspective view of a microcapillary dispensing from the flexible pouch in accordance with an embodiment of the present disclosure.
Figure 5A:
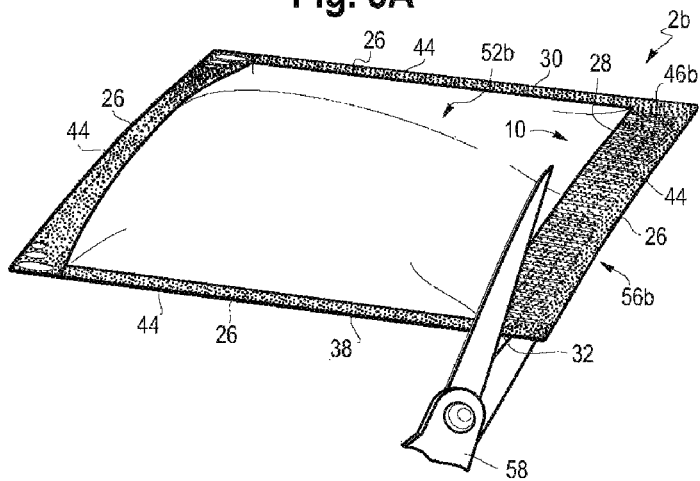
FIG. 5A is a perspective view of the removal of a release member in accordance with an embodiment of the present disclosure.
Figure 5B:
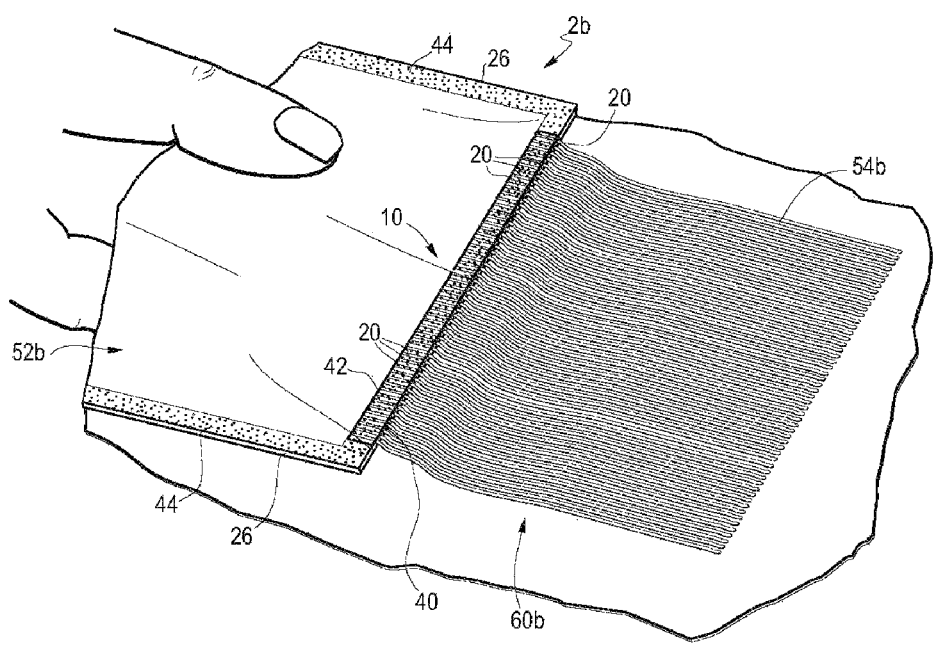
FIG. 5B a perspective view of microcapillary dispensing from the flexible pouch in accordance with an embodiment of the present disclosure.

In an embodiment shown in FIGS. 5A-5B, a flexible pouch 2b includes the common peripheral edge 26 which defines a polygon, such as a 4-sided polygon (rectangle, square, diamond). In this embodiment, the first side 28 of the microcapillary strip 10 is located at a first side 30 of the 4-sided polygon. The second side 32 of the microcapillary strip 10 is located at a parallel side 38 of the 4-sided polygon. As shown in FIGS. 5A-5B, the first side 30 of the 4-sided polygon is parallel to, and does not intersect, the second side 38 of the 4-sided polygon.

The microcapillary strip 10 may or may not extend along the entire length of one side of the polygon. FIGS. 5A, 5B show microcapillary strip 10 extending along only a portion of the length of one side of the polygon.

Flexible pouches 2a, 2b each have a respective storage compartment 52a, 52b. As the first film 22 and the second film 24 are flexible, so too is each pouch 2a, 2b a flexible pouch.

In an embodiment, a fill inlet is located on the peripheral edge. The fill inlet is closable and permits filling of the storage compartment with a liquid 54. Alternatively, a portion of the peripheral edge 26 remains unsealed and a fill member adds liquid into the storage compartment. After the storage compartment is filled with liquid, the unsealed portion of the peripheral edge is subsequently sealed to form a sealed and closed flexible pouch.

The peripheral seal 44 forms a hermetic seal around the periphery of flexible pouch 2a and 2b. Each of flexible pouch 2a and 2b is a sealed and closed flexible pouch. The peripheral seal 44 forms a sealed and closed flexible pouch 2a and/or 2b each pouch having a storage compartment. In an embodiment, a liquid is present in the storage compartment. Nonlimiting examples of suitable liquids include fluid comestibles (beverages, condiments, salad dressings, flowable food), liquid or fluid medicaments, aqueous plant nutrition, household and industrial cleaning fluids, disinfectants, moisturizers, lubricants, surface treatment fluids such as wax emulsions, polishers, floor and wood finishes, personal care liquids (oils, creams, lotions, gels), etc.

In an embodiment, the matrix 18 of the microcapillary strip 10 is composed of a material having a material surface tension (M-surface tension) from 15 dyn/cm, or 17 dyn/cm, or 20 dyn/cm, or 22 dyn/cm, or 23 dyn/cm to 25 dyn/cm, or 27 dyn/cm, or 29 dyn/cm, or 30 dyn/cm, or 32 dyn/cm. The liquid 54 in the storage compartment has a liquid surface tension (L-surface tension) greater than or equal to 70 dyn/cm, or 71 dyn/cm, or 72 dyn/cm, or 75 dyn/cm, or 77 dyn/cm to 80 dyn/cm, or 85 dyn/cm, or 90 dyn/cm.

Nonlimiting examples of materials having an M-surface tension from 15-32 dyn/cm are provided in Table 1 below.

TABLE 1

Material Surface Tension

| Material | M-Surface Tension (dyn/cm) |
|---|---|
| Poly(hexafluoropropylene) | 16.9 |
| Poly t-butyl methacrylate (PtBMA) | 18.1 |
| Fluorinated ethylene propylene (FEP) | 19.1 |
| Polytetrafluoroethylene (PTFE) | 19.4 |
| Polydimethylsiloxane (PDMS) | 20.1 |
| Hexatriacontane | 20.6 |
| Paraffin | 24.8 |
| Polytrifluoroethylene | 26.5 |
| Polyisobutylene (PIB, butyl rubber) | 27 |
| Polybutadiene | 29.3 |
| Poly n-butyl methacrylate (PnBMA) | 29.8 |
| Polypropylene (PP) | 30.5 |
| Polychlorotrifluoroethylene (PCTFE) | 30.8 |
| Polyethylene (PE) | 31.6 |
| Polyvinylidene fluoride (PVDF) | 31.6 |
| Elite 5100 etylene/octene copolymer | 32 |

Nonlimiting examples of liquids having an L-surface tension from greater than or equal to 70 dyn/cm to 90 dyn/cm are provided in Table 2 below.

TABLE 2

Liquid L-surface tensions

| Liquid | Temp (° C.) | L-surface tension (dyn/cm) |
|---|---|---|
| Water | 25 | 71.97 |
| Water | 0 | 75.64 |
| Sucrose (55%) + water | 20 | 76.45 |
| Sodium chloride 6.0M aqueous solution | 20 | 82.55 |

In an embodiment, the material for matrix 18 has an M-surface tension from 15 dyn/cm to 32 dyn/cm (as disclosed above) and is selected from an ethylene-based polymer, or a propylene-based polymer. The liquid has an L-surface tension from greater than or equal to 70 dyn/cm to 85 dyn/cm, and the liquid is an aqueous-based solution.

In an embodiment, the matrix 18 of the microcapillary strip 10 is composed of a material having an M-surface tension from greater than 32 dyn/cm, or 35 dyn/cm, or 37 dyn/cm to 40 dyn/cm, or 43 dyn/cm, or 45 dyn/cm, or 47 dyn/cm, or 50 dyn/cm. The liquid 54 has an L-surface tension less than 70 dyn/cm, or from 15 dyn/cm, or 20 dyn/cm, or 25 dyn/cm, or 30 dyn/cm, or 35 dyn/cm, or 40 dyn/cm to 50 dyn/cm, or 55 dyn/cm, or 60 dyn/cm, or 65 dyn/cm, or 69 dyn/cm, or less than 70 dyn/cm. In a further embodiment, the liquid 54 having an L-surface tension from 15 dyn/cm to less than 70 dyn/cm is a non-aqueous liquid.

Nonlimiting examples of materials having an M-surface tension from greater than 32 dyn/cm to 50 dyn/cm are provided in Table 3 below.

TABLE 3

Material Surface Tension

| Material | M-Surface Tension (dyn/cm) |
|---|---|
| Amplify IO 3801 Na-based ionomers | 34 |
| Primacor 1410 ethylene/acrylic acid copolymer, 9.7 wt % acrylic acid) | 34 |
| Nylon 8,8/9,9 | 34 |
| Polystyrene | 34 |
| Polyvinyl acetate | 35.3 |
| Polyvinyl alcohol | 37 |
| Polymethyl methacrylate (PMMA) | 37.5 |
| Polyvinyl chloride | 37.9 |
| Polyethylene terephthalate (PET) | 39 |
| Nylon 6,6 | 42.2 |

Surface treatment methods can be applied in order to modify the M-surface tensions of the materials listed in Tables 1 and 3. Nonlimiting examples of liquids having an L-surface tension from 30 dyn/cm to less than 70 dyn/cm are provided in Table 4 below.

TABLE 4

Liquid L-surface tensions

| Liquid | Temperature ° C. | Surface tension (dyne/cm) |
|---|---|---|
| Acetic acid | 20 | 27.6 |
| Acetic acid (10.0%) + Water | 30 | 54.56 |
| Acetone | 20 | 23.7 |
| Diethyl ether | 20 | 17 |

TABLE 4-continued

Liquid L-surface tensions

| Liquid | Temperature ° C. | Surface tension (dyne/cm) |
|---|---|---|
| Ethanol | 20 | 22.27 |
| Ethanol (11.1%) + Water | 25 | 46.03 |
| Glycerol | 20 | 63 |
| n-Hexane | 20 | 18.4 |
| Isopropanol | 20 | 21.7 |
| Methanol | 20 | 22.6 |
| n-Octane | 20 | 21.8 |
| Toluene | 25 | 27.73 |
| Sodium oleate (soap) solution in water* | 20 | 25 |

*Soap solution used in the examples.

4. Release Member

In an embodiment, the flexible pouch includes a release member. The release member includes a portion of the sealed microcapillary segment. Removal of the release member from the flexible pouch exposes the channels of the microcapillary strip.

The release member is a detachable portion of the flexible pouch. The release member can be completely (or wholly) detached from the flexible pouch. Alternatively, the release member can be partially detached, with a portion of the release member remaining attached to the flexible pouch. The purpose of the release member is two-fold. First, the release member blocks, or otherwise prevents, the flow of liquid from the storage compartment during storage of the flexible pouch. Second, detachment, or removal, of the release member from the flexible pouch exposes the channels, and thereby enables dispensing of the liquid from the flexible pouch through the microcapillary strip.

Figure 4:
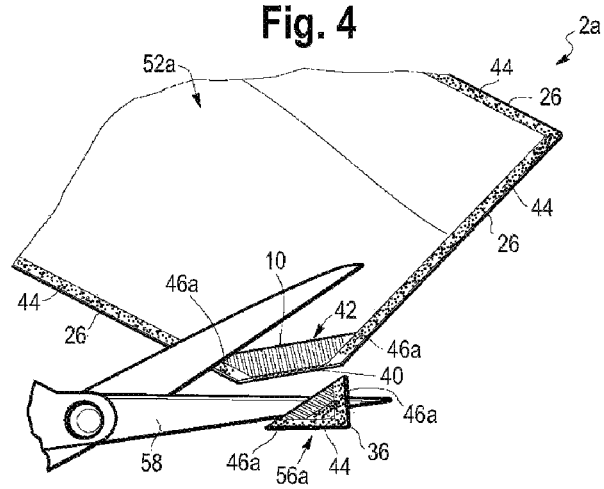
FIG. 4 is a perspective view of the removal of a release member in accordance with an embodiment of the present disclosure.

FIGS. 4 and 5A show the detachment of release member 56a, 56b from respective flexible pouches 2a, 2b. Detachment is actuated by way of hand (manually), tool, machine, and combinations thereof. In an embodiment, the release member 56a, 56b is detached manually (by hand) from respective flexible pouch 2a, 2b, with a person cutting a respective portion of the sealed microcapillary segment 46a, 46b with a sharp object such as a blade, a knife, or a scissors 58, as shown in FIGS. 4 and 5A.

As shown in FIG. 4, detachment of the release member 56a removes a portion of the sealed microcapillary segment 46a and exposes the outer edge 40 of the microcapillary strip 10 to the external environment. Once a portion of the sealed microcapillary segment 46a, is removed from the pouch 2a, the exposed channels 20 place the interior of storage compartment 52a in fluid communication with exterior of the flexible pouch 2a. Detachment of the release member 56b (FIG. 5A) from the flexible pouch 2b removes a portion of the sealed microcapillary segment 46b to expose channels 20 in a similar manner.

In an embodiment, the flexible pouch includes a squeezing force (or a compression force) imparted upon the storage compartment. A flow of the liquid passes through the exposed channels of the microcapillary strip and passes out of the flexible pouch.

In an embodiment, a person's hand imparts a squeezing force upon the storage compartment 52a (or 52b), as shown in FIGS. 5 and 5B. The squeezing force dispenses the liquid (54a, 54b) through the channels 20 and out of respective pouches 2a, 2b.

In an embodiment, a squeezing force imparted with a person's hand on the storage compartment 52a dispenses a spray pattern 60a of the liquid 54a from the flexible pouch 2a as shown in FIG. 5. The spray pattern 60a can be advantageously controlled by adjusting the amount of squeeze force imparted upon the storage compartment 52a. In this way, the flexible pouch 2a surprisingly delivers a controlled spray pattern of liquid without the need for a rigid spray component. The profile of spray 60a can be designed by the configuration of the channels 20 in the microcapillary strip 10. Channels 20 with a relatively smaller diameter, D, will dispense a fine spray of the liquid when compared to channels 20 with a relatively larger diameter, D. FIG. 5 shows the dispensing of a low viscosity liquid 56a, (such as a water-based beverage), as a fine and controlled spray 60a and received in a container 62 (such as a cup).

In an embodiment, a squeezing force imparted with a person's hand on the storage compartment 52b dispenses a flow pattern 60b of the liquid 54b as shown in FIG. 5B. The flow pattern 60b can be advantageously controlled by adjusting the amount of squeeze force imparted upon the storage compartment 52b. In this way, the flexible pouch 50b surprisingly delivers a controlled application of liquid without the need for a rigid spray component. The diameter, D, of the channels 20 are configured so the profile of spray 60b delivers, or otherwise dispenses, a smooth and even application of a viscous liquid 56b, such as a high viscosity liquid, a lotion or a cream, onto a surface, such as a person's skin, as shown in FIG. 5B.

5. Edge Offset Distance

The present disclosure provides another flexible pouch. In an embodiment, a flexible pouch is provided and includes opposing flexible films. The opposing flexible films define a common peripheral edge. A microcapillary strip is located at an edge offset distance between the opposing flexible films. The microcapillary strip is sealed between the opposing flexible films. A first side of the microcapillary strip is located at a first side of the common peripheral edge and a second side of the microcapillary strip is located at a second side of the common peripheral edge. A peripheral seal extends along at least a portion of the common peripheral edge.

In an embodiment, the peripheral seal includes a sealed microcapillary segment.

Flexible pouch 102 (FIGS. 6-8), flexible pouch 202 (FIGS. 9-10), and flexible pouch 302 (FIGS. 11-13) each include a microcapillary strip located at an edge offset distance. The "edge offset distance," or "EOD," is a length from the peripheral edge to an interior portion of the flexible films. The edge offset distance, EOD, can be from greater than zero millimeter (mm), or 1 mm, or 1.5 mm, or 2.0 mm, or 2.5 mm, or 3.0 mm, or 3.5 mm to 4.0 mm, or 4.5 mm, or 5.0 mm, or 6.0 mm, or 7.0 mm, or 9.0 mm, or 10.0 mm, or 15.0 mm, or 20.0 mm, or 40.0 mm, or 60.0 mm, or 80.0 mm, or 90.0 mm, or 100.0 mm.

Figure 6:
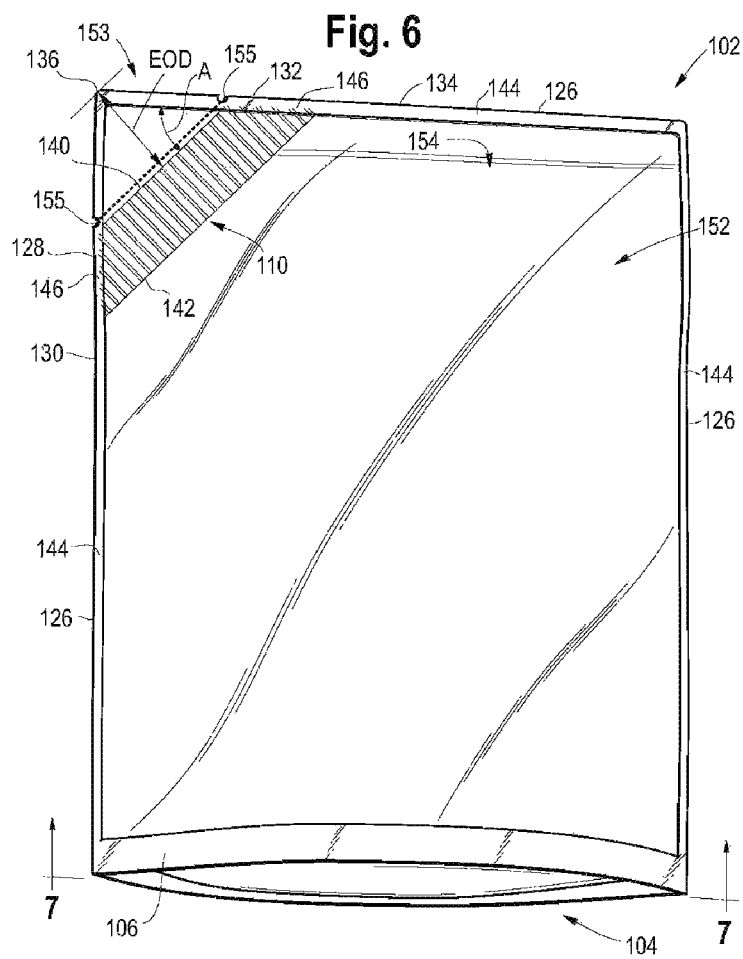
FIG. 6 is a perspective view of a flexible pouch with a microcapillary dispensing system in accordance with another embodiment of the present disclosure.
Figure 7:
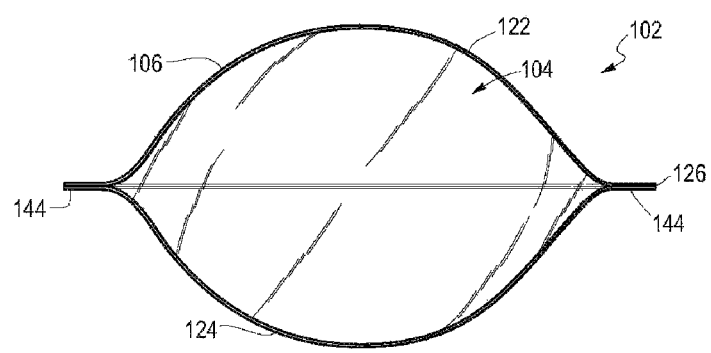
FIG. 7 is a sectional view taken along line 7-7 of FIG. 6.
Figure 8:
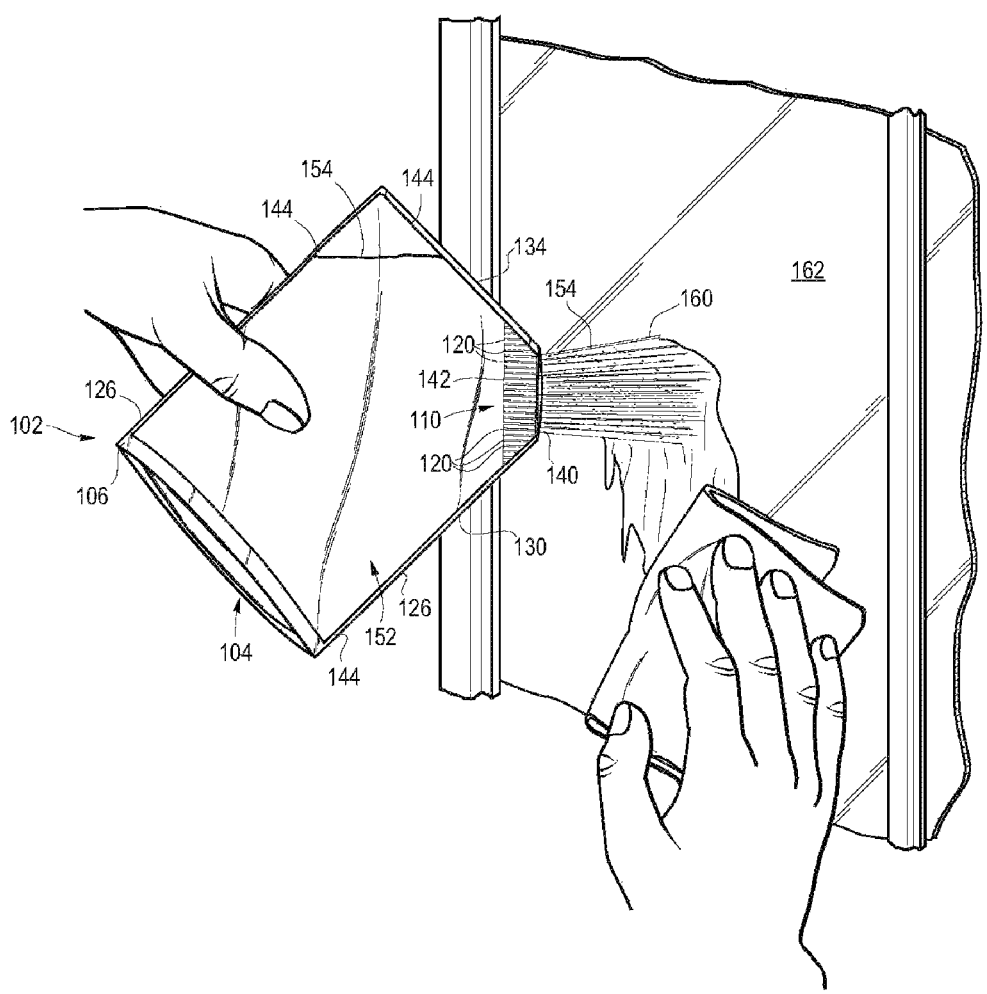
FIG. 8 is a perspective view of microcapillary dispensing from the flexible pouch in accordance with another embodiment of the present disclosure.

FIGS. 6-8 show an embodiment, wherein the flexible pouch is flexible stand-up pouch (or SUP) 102. The SUP 102 includes first flexible film 122, second flexible film 124, and a gusset panel 104. The gusset panel 104 joins the first flexible film 122 to the second flexible film 124 along a bottom of the pouch. The flexible films 122, 124 and the gusset panel 104 form a hermetically sealed storage compartment 152.

The gusset panel 104 is made from the same material as the flexible films 122, 124. The gusset panel 104 joins the flexible film 122 to the flexible film 124 along a bottom of the pouch to form a base for the flexible pouch. The gusset panel 104 includes a gusset rim 106. The gusset rim 106 supports the flexible pouch 102 and enables the flexible pouch to stand in an upright position. The gusset panel 104 is formed by folding, shaping, and sealing a portion of the first flexible film 122 with a portion of the second flexible film 124. Nonlimiting procedures for joining the gusset panel 104 and the flexible films 122, 124 include heat seal, ultrasonic seal, impulse, radio frequency (RF) sealing, weld, adhesive seal, and combinations thereof.

The flexible films 122, 124 define a common peripheral edge 126, as previously disclosed herein. The microcapillary strip 110 is placed at an edge offset distance, EOD, between opposing flexible films 122, 124. The distance from the corner 136 to the outer edge 140 of the microcapillary strip, is the edge offset distance shown as length EOD in FIG. 6. The EOD is perpendicular to outer edge 140. In an embodiment, the EOD is from greater than 0 mm, or 1.0 mm, or 1.5 mm, or 2.0 mm, or 3.0 mm, or 4.0 mm, or 5.0 mm, or 10.0 mm to 15.0 mm, or 20.0 mm, or 25.0 mm, or 30 mm.

The common peripheral edge 126 defines a 4-sided polygon (rectangle, square, diamond). In an embodiment, the first side 128 of the microcapillary strip 110 is located at a first side 130 of the 4-sided polygon. The second side 132 of the microcapillary strip 110 is located at an intersecting side 134 of the 4-sided polygon. As shown in FIGS. 6-8, the second side 134 of the 4-sided polygon intersects the first side 130 of the 4-sided polygon, the intersection being corner 136.

The microcapillary strip 110 has an outer edge 140 and an inner edge 142. In an embodiment, the outer edge 140 forms angle A at the corner 136, as shown in FIG. 6. In a further embodiment, angle A is 45°.

The microcapillary strip 110, located at the edge offset distance, forms a storage compartment 152 and a corner pocket 153 shown in FIG. 6. The microcapillary strip 110 separates the storage compartment 152 from the corner pocket 153. A peripheral seal 144 forms a closed and sealed flexible pouch 102. The peripheral seal 144 includes at least one sealed microcapillary segment 146.

The corner pocket 153 functions as the release member for the pouch 102. Hence, the corner pocket 153 is a detachable portion of the flexible pouch 102. The corner pocket 153 has the same two-fold purpose as previously discussed for the release member. Since the corner pocket 153 is the result of the edge offset distance between the microcapillary strip 110 and the peripheral edge 126, the corner pocket 153 may or may not include a portion of the sealed microcapillary segment.

In an embodiment, the corner pocket 153 includes a portion of the peripheral seal 144 but does not include a portion of the sealed microcapillary segment 146.

In an embodiment, the pocket 153 includes cut-outs (or notches) 155 in the peripheral seal 144. Cut-outs 155 enable ready removal of the corner pocket 153. In this way, corner pocket 153 enables, or otherwise promotes, tearing, by hand, the corner pocket 153 from the flexible pouch 102. It is understood corner pocket 153 also may be removed by cutting with a blade or scissors, for example.

In an embodiment, a squeezing force is imparted by hand upon the storage compartment 152. The squeezing force dispenses liquid 154 through the exposed channels 120 and out of the flexible pouch 102. The exposed channels 120 dispense a spray pattern 160 of the liquid 154, as shown in FIG. 8. FIG. 8 shows the dispensing of a low viscosity liquid 154 (such as a water-based cleaning solution), as a fine and controlled spray. The spray pattern 160 and the spray flow intensity can be advantageously controlled by adjusting the amount of squeeze force imparted upon the storage compartment 152a, as previously discussed. In this way, the flexible pouch 102 surprisingly and advantageously provides a flexible pouch and dispensing system that can be operated entirely by hand—i.e., hand removal of corner pocket 153, hand control (squeeze) of spray pattern 160, and hand operation of the wiping of a surface to be cleaned 162.

FIG. 8A provides an embodiment, wherein the flexible pouch includes a microcapillary strip having non-parallel channels. Stand-up pouch 102a includes common peripheral edge 126a which defines a 4-sided polygon (rectangle, square, diamond). In an embodiment, the first side 128a of the microcapillary strip 110a is located at a first side 130a of the 4-sided polygon. The second side 132a of the microcapillary strip 110a is located at an intersecting side 134a of the 4-sided polygon.

In FIG. 8A, the microcapillary strip 110a includes non-parallel channels 120a. With the release member (a pocket 153a, not shown), removed, a squeezing force imparted by a person's hand upon storage compartment 152a dispenses liquid 154a through the exposed non-parallel channels 120a and out of the flexible pouch 102a. The non-parallel channels 120a are exposed along the outer edge 140a and are configured to dispense a fan spray pattern 160a of the liquid 154a, as shown in FIG. 8A. When compared to the spray profile 160 (FIG. 8), the fan spray 160a (FIG. 8A) delivers a disperse, or otherwise wide area (fan) spray pattern 160a. The fan spray pattern 160a is suitable for many applications. An nonlimiting application for fan spray pattern 160a is for watering a plant 164, as shown in FIG. 8A.

In an embodiment, the matrix 118 of microcapillary strip 110 and/or 110a is composed of a material having an M-surface tension from 15 dyn/cm, or 17 dyn/cm, or 20 dyn/cm, or 22 dyn/cm, or 23 dyn/cm to 25 dyn/cm, or 27 dyn/cm, or 29 dyn/cm, or 30 dyn/cm, or 32 dyn/cm. The liquid 154 in the storage compartment has an L-surface tension greater than or equal to 70 dyn/cm, or 71 dyn/cm, or 72 dyn/cm, or 75 dyn/cm, or 77 dyn/cm to 80 dyn/cm, or 85 dyn/cm, or 90 dyn/cm.

Nonlimiting examples of suitable materials for the matrix 118 with an M-surface tension from 15 dyn/cm to 32 dyn/cm are provided in Table 1. Nonlimiting examples of suitable liquids having an L-surface tension from greater than 70 dyn/cm to 90 dyn/cm are provided in Table 2. In an embodiment, the material for matrix 118 has an M-surface tension from 15 dyn/cm to 32 dyn/cm (as disclosed above) and is selected from an ethylene-based polymer, or a propylene-based polymer. The liquid 154 has an L-surface tension from greater than or equal to 70 dyn/cm to 85 dyn/cm, and the liquid is an aqueous-based solution.

In an embodiment, the material for matrix 118 of the microcapillary strip 110 and/or 110a is composed of a material having an M-surface tension from greater than 32 dyn/cm, or 35 dyn/cm, or 37 dyn/cm to 40 dyn/cm, or 43 dyn/cm, or 45 dyn/cm, or 47 dyn/cm, or 50 dyn/cm. The liquid 154 has an L-surface tension less than 70 dyn/cm, or from 15 dyn/cm, or 20 dyn/cm, or 25 dyn/cm, or 30 dyn/cm, or 35 dyn/cm, or 40 dyn/cm to 50 dyn/cm, or 55 dyn/cm, or 60 dyn/cm, or 65 dyn/cm, or 69 dyn/cm, or less than 70 dyn/cm. In a further embodiment, the liquid 154 having an L-surface tension from 15 dyn/cm to less than 70 dyn/cm is a non-aqueous liquid.

Nonlimiting examples of materials with an M-surface tension from greater than 32 dyn/cm to 50 dyn/cm are provided at Table 3. Nonlimiting examples of liquids with an L-surface tension from 15 dyn/cm to less than 70 dyn/cm are provided at Table 4.

FIGS. 9-10 provide an embodiment wherein the flexible pouch is a flexible stand-up pouch (or SUP) 202. The SUP 202 includes first flexible film 222, second flexible film 224, a gusset panel 204, and a gusset rim 206. The gusset panel 204 includes gusset rim 206 and can be any gusset panel as previously discussed herein. The gusset panel 204 joins the first flexible film 222 to the second flexible film 224 as previously discussed. The flexible films 222, 224 and the gusset panel 204 form a hermetically sealed storage compartment 252.

An indicia 208 can be printed, or otherwise applied, on the outer surface of flexible film 222 and/or flexible film 224. The indicia 208 can be marketing or branding content, or can be information related to, or otherwise describing, the contents of the SUP 202, such as a cross designating first aid or a medicament.

The flexible films 222, 224 define a common peripheral edge 226, as previously disclosed herein. The microcapillary strip 210 is placed at an edge offset distance, EOD, between opposing flexible films 222, 224, as shown in FIG. 9.

The common peripheral edge 226 defines a 4-sided polygon (rectangle, square, diamond). In an embodiment, the first side 228 of the microcapillary strip 210 is located at a first side 230 of the 4-sided polygon. The second side 232 of the microcapillary strip 210 is located at a parallel side 238 of the 4-sided polygon. As shown in FIG. 9, the second side 238 of the 4-sided polygon is parallel to, and does not intersect the first side 230 of the 4-sided polygon.

The microcapillary strip 210 has an outer edge 240 and an inner edge 242. The distance from the top peripheral edge 226, to the outer edge 240 is the edge offset distance, shown as distance EOD in FIG. 9.

In an embodiment, the EOD is from greater than 0 mm to 30 mm.

In an embodiment, the EOD is from 1%, or 5%, or 10%, or 15%, or 20%, or 25% to 30%, or 35%, or 40%, or 45%, or 50% the length (the length being the distances from the top of the SUP to the gusset panel 204) of the SUP 202.

The microcapillary strip 210, located at the edge offset distance, EOD, forms a storage compartment 252 and a long pocket 253. The microcapillary strip 210 separates the storage compartment 252 from the long pocket 253. A peripheral seal 244 forms a closed and sealed flexible pouch 202. The peripheral seal 244 includes at least one sealed microcapillary segment 246.

The long pocket 253 functions as the release member for the pouch 202. Hence, the pocket 253 is a detachable portion of the flexible pouch 202. The long pocket 253 has the same two-fold purpose as previously discussed for the release member. Since the long pocket 253 is the result of the edge offset distance between the microcapillary strip 210 and the peripheral edge 226, the long pocket 253 may or may not include a portion of the sealed microcapillary segment.

In an embodiment, the long pocket 253 includes a portion of the peripheral seal 244, but does not include a portion of the sealed microcapillary segment 246, as shown in FIG. 9.

In an embodiment, the long pocket 253 includes cut-outs (or notches) 255 in the peripheral seal 244. Cut-outs 255 enable ready removal of the long pocket 253. In this way, long pocket 253 enables, or otherwise promotes, tearing, by hand, the long pocket 253 from the flexible pouch 202.

In an embodiment, a squeezing force is imparted by hand upon the storage compartment 252. The squeezing force dispenses liquid 254 through outer edge 240 and through the exposed channels 220 and out of the pouch 202. The exposed channels 220 dispense a flow pattern 260 of the liquid 254, as shown in FIG. 10. FIG. 10 shows the dispensing of a high viscosity liquid 254, (such as a medicament in cream form, a cream for wound treatment), as an even and uniform controlled layer of liquid. The flow pattern 260 and the flow intensity can be advantageously controlled by adjusting the amount of squeeze force imparted upon the storage compartment 252, as previously discussed. In this way, the flexible pouch 202 surprisingly and advantageously provides a flexible pouch and dispensing system that can be operated entirely by hand—i.e., hand removal of long pocket 253, hand control (squeeze) of flow pattern 260, and hand treatment of wound 262.

Figure 11:
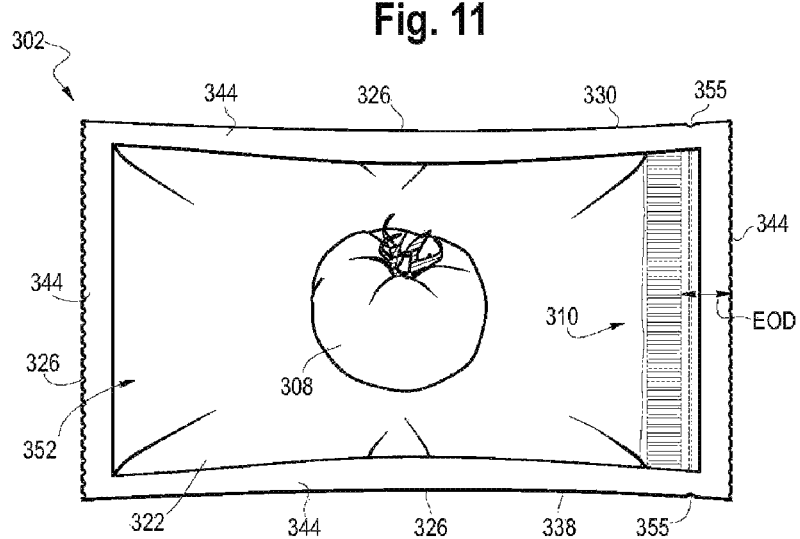
FIG. 11 is a top plan view of a flexible pouch with a microcapillary dispensing system in accordance with an embodiment of the present disclosure.
Figure 12:
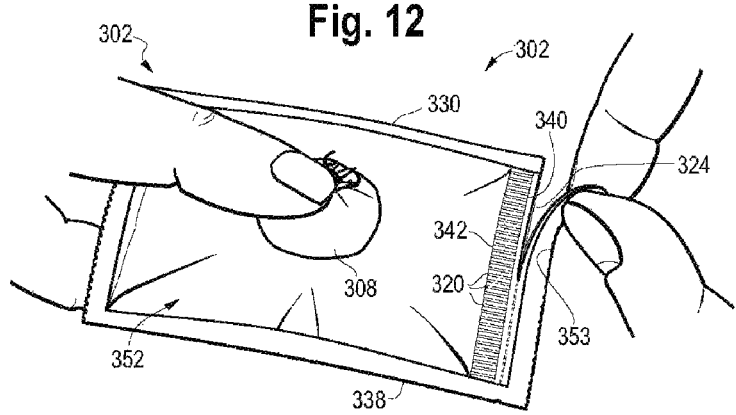
FIG. 12 is a perspective view of a pocket segment in accordance with an embodiment of the present disclosure.
Figure 13:
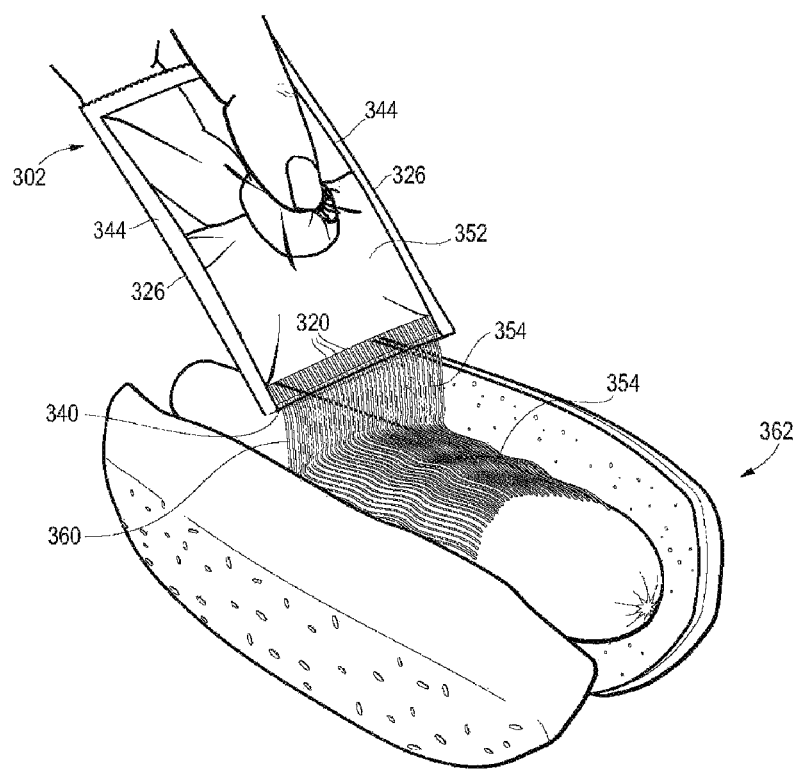
FIG. 13 is a perspective view of microcapillary dispensing from the flexible pouch in accordance with an embodiment of the present disclosure.

FIGS. 11-13 show another embodiment wherein flexible pouch 302 includes a long pocket 353. The edge offset distance, EOD, is the distance between the peripheral seal 344 and the edge 340 of the microcapillary strip 310, as shown in FIG. 11.

Cut-outs (or notches) 355 in the peripheral seal 344 enable ready removal of the long pocket 353. The long pocket 353 and cut-outs 355 enable hand opening of the pouch 302 by way of hand tearing, or finger tearing, the long pocket 353 from the pouch 302.

An indicia 308 can be printed, or otherwise applied, on the outer surface of flexible film 322 and/or flexible film 324. The indicia 308 can be marketing or branding content, or can be information related to, or otherwise describing, the contents of the SUP 302 (such as ketchup, for example).

In an embodiment, a squeezing force is imparted by hand upon the storage compartment 352. The squeezing force dispenses liquid 354 through the exposed channels 320 and out of the pouch 302. The exposed channels 320 dispense a flow pattern 360 of the liquid 254, as shown in FIG. 13. FIG. 13 shows the dispensing of a high viscosity liquid 354, (such as a comestible, such as a condiment), as an even and uniform controlled layer. The flow pattern 360 and the flow intensity can be advantageously controlled by adjusting the amount of squeeze force imparted upon the storage compartment 352, as previously discussed. In this way, the flexible pouch 302 surprisingly and advantageously provides a flexible pouch and food dispensing system that can be operated entirely by hand—i.e., hand removal of long pocket 353, hand control (squeeze) of flow pattern 360, and simplified and controlled dispensing of flowable comestible 354 (such as a condiment) a onto a food item 362, as shown in FIG. 13. Flexible pouch 302 advantageously provides controlled and measured dispensing of the comestible, reduces food spillage of the comestible, reduces or eliminates food mess from the comestible, and/or reduces or eliminates waste of comestible 354.

In an embodiment, any of the foregoing flexible pouches may include a closure. The closure covers the exposed channels after the release member is removed or the outer edge of the microcapillary strip is otherwise exposed to the external environment. Nonlimiting examples of suitable closures for the present flexible pouch include a Ziploc-type closure, hook and loop material (i.e., Velcro), an adhesive strip (such as packaging tape, for example), and flexible material hingedly attached to the flexible pouch for placement over the exposed channels. The release member may also be configured to include a closure.

Any of the foregoing flexible pouches can have a storage compartment volume from 1.0 milliliter (ml), or 10 ml, or 100 ml, or 500 ml to 1 liter (L), or 10 L, or 100 L, or 1000 L.

Any of the foregoing flexible pouches may be produced as disclosed in WO 2017/003859, published 5 Jan. 2017 and WO 2017/003865, published 5 Jan. 2017, the entire content of each incorporated by reference herein.

6. Three-Sided Seal

The present disclosure provides another flexible pouch. In an embodiment, a flexible pouch is provided and includes opposing flexible films. The flexible films define a common peripheral edge. A microcapillary strip is sealed between the opposing flexible films. The microcapillary strip includes opposing sides and opposing edges. A peripheral seal extends along at least a portion of the common peripheral edge. The peripheral seal includes (i) a side seal along each side of the microcapillary strip, and (ii) an edge seal along an outer edge of the microcapillary strip. The peripheral seal forms a closed flexible pouch having a storage compartment.

Figure 14:
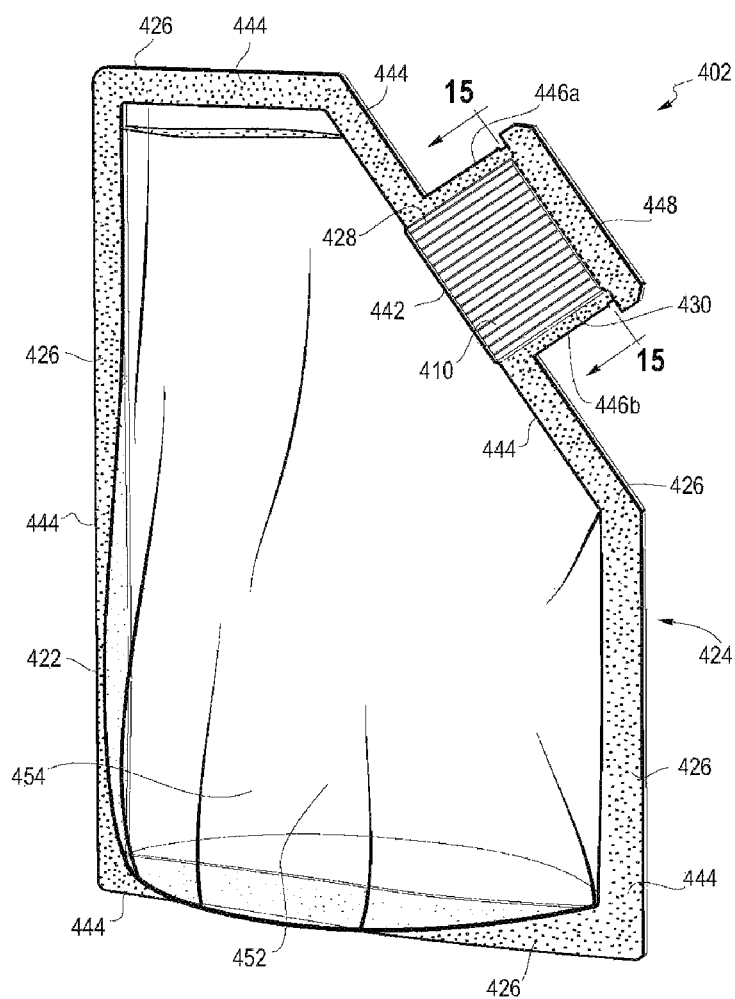
FIG. 14 is a perspective view of a flexible pouch in accordance with an embodiment of the present disclosure.
Figure 15:
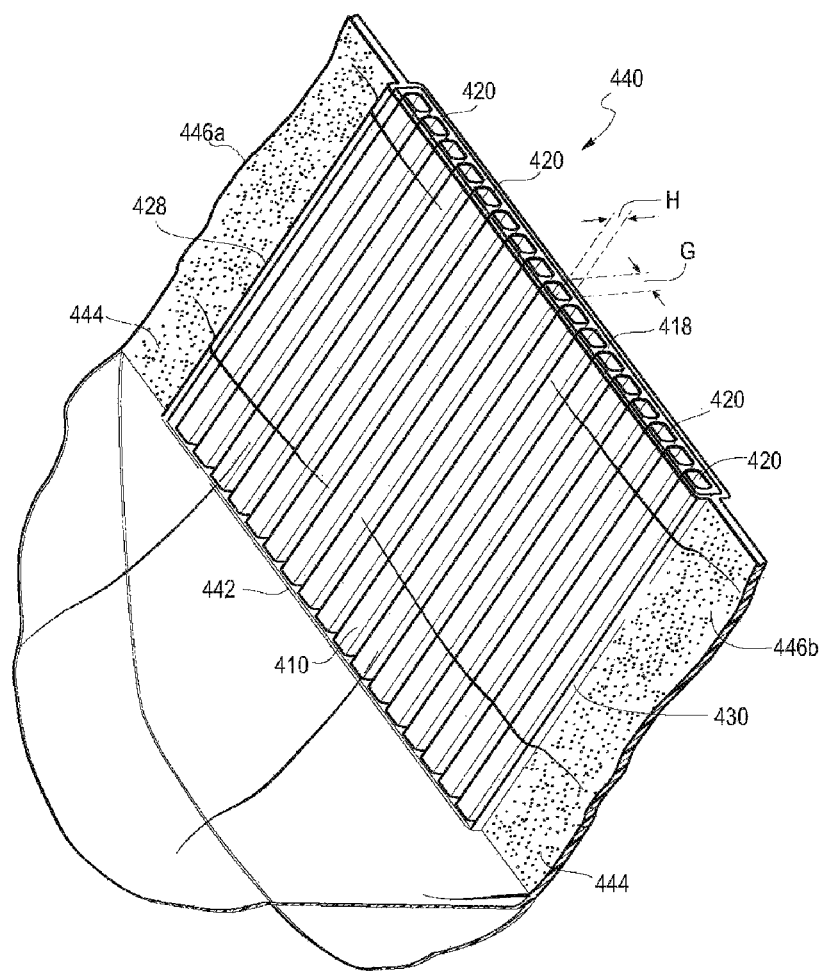
FIG. 15 is an enlarged perspective view of the microcapillary strip taken along line 15-15 of FIG. 14.
Figure 16:
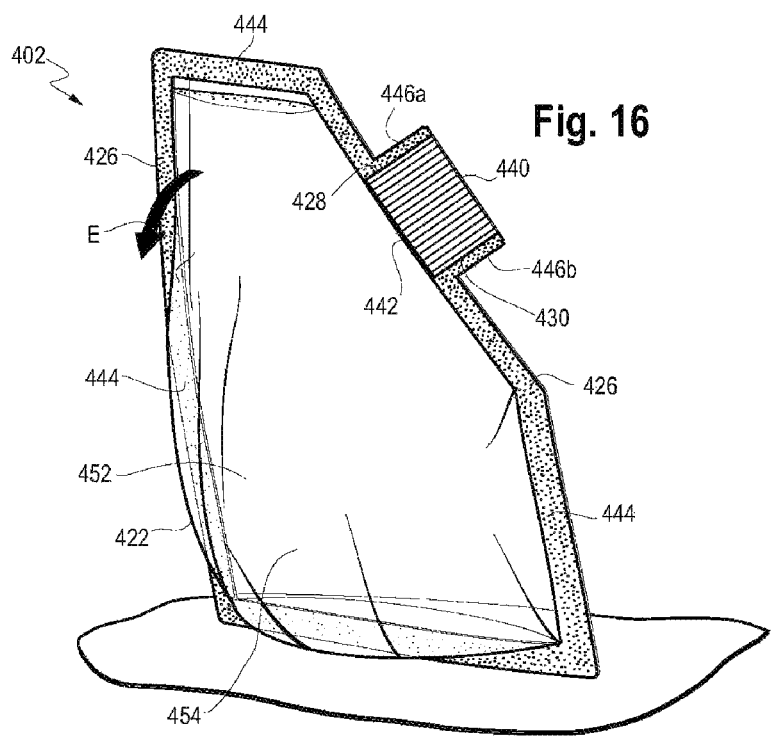
FIG. 16 is a perspective view of the opened flexible pouch of FIG. 14.

FIGS. 14-16 show flexible pouch 402. Flexible pouch 402 includes microcapillary strip 410 sandwiched and sealed between opposing first flexible film 422 and second flexible film 424. The flexible films 422, 424 share a common peripheral edge 426. The microcapillary strip 410 has opposing sides, first side 428 and second side 430. The microcapillary strip 410 has opposing edges, outer edge 440 and inner edge 442.

A peripheral seal 444 extends along a portion of (or along the entirety of) the common peripheral edge 426. The peripheral seal 444 includes side seals 446a and 446b. Side seal 446a extends along side 428 of the microcapillary strip. Side seal 446b extends along side 430 of the microcapillary strip.

The peripheral seal 444 also includes an edge seal 448. The edge seal 448 extends along the outer edge 440 of the microcapillary strip. As shown in FIGS. 14-15, the side seals 446a, 446b and the edge seal 448 abut against respective microcapillary sides 428, 430 and outer edge 440 without collapsing the channels 420 of the microcapillary strip 410.

In an embodiment, the edge seal 448 is a release member that is a tear seal. FIG. 15 shows the exposed outer edge 440 of the microcapillary strip after removal of the edge seal 448.

In an embodiment, the matrix 418 of microcapillary strip 410 is composed of a material having an (M-surface tension from 15 dyn/cm, or 17 dyn/cm, or 20 dyn/cm, or 22 dyn/cm, or 23 dyn/cm to 25 dyn/cm, or 27 dyn/cm, or 29 dyn/cm, or 30 dyn/cm, or 32 dyn/cm. The liquid 454 in the storage compartment has an L-surface tension) greater than or equal to 70 dyn/cm, or 71 dyn/cm, or 72 dyn/cm, or 75 dyn/cm, or 77 dyn/cm to 80 dyn/cm, or 85 dyn/cm, or 90 dyn/cm. Applicant discovered a flexible pouch with a microcapillary strip having a matrix material with an M-surface tension from 15 dyn/cm to 32 dyn/cm mated with a liquid having a an L-surface tension from greater than 70 dyn/cm to 90 dyn/cm yields a non-wetting surface interface between the stored liquid and the channels 420. The non-wetting interface holds the liquid within the storage chamber and reduces leak when the open flexible container is spilled or tipped.

Nonlimiting examples of suitable materials for the matrix 418 with an M-surface tension from 15 dyn/cm to 32 dyn/cm are provided in Table 1. Nonlimiting examples of suitable liquids having an L-surface tension from greater than 70 dyn/cm to 90 dyn/cm are provided in Table 2. In an embodiment, the material for matrix 418 has an M-surface tension from 15 dyn/cm to 32 dyn/cm (as disclosed above) and is selected from an ethylene-based polymer, or a propylene-based polymer. The liquid 454 has an L-surface tension from greater than or equal to 70 dyn/cm to 85 dyn/cm, and the liquid is an aqueous-based solution.

In an embodiment, the material for matrix 418 of the microcapillary strip 410 is composed of a material having an M-surface tension from greater than 32 dyn/cm, or 35 dyn/cm, or 37 dyn/cm to 40 dyn/cm, or 43 dyn/cm, or 45 dyn/cm, or 47 dyn/cm, or 50 dyn/cm. The liquid 454 has an L-surface tension less than 70 dyn/cm, or from 15 dyn/cm, or 20 dyn/cm, or 25 dyn/cm, or 30 dyn/cm, or 35 dyn/cm, or 40 dyn/cm to 50 dyn/cm, or 55 dyn/cm, or 60 dyn/cm, or 65 dyn/cm, or 69 dyn/cm, or less than 70 dyn/cm. In a further embodiment, the liquid 454 having an L-surface tension from 15 dyn/cm to less than 70 dyn/cm is a non-aqueous liquid.

Nonlimiting examples of materials with an M-surface tension from greater than 32 dyn/cm to 50 dyn/cm are provided at Table 3. Nonlimiting examples of liquids with an L-surface tension from 15 dyn/cm to less than 70 dyn/cm are provided at Table 4. Applicant discovered a flexible pouch with a microcapillary strip having a matrix material with an M-surface tension from greater than 32 dyn/cm to 50 dyn/cm mated with a liquid having a an L-surface tension 15 dyn/cm to less than 70 dyn/cm yields a non-wetting surface interface between the stored liquid and the channels. The non-wetting interface holds the liquid within the storage chamber and reduces leak when the open flexible container is spilled or tipped.

Figure 17:
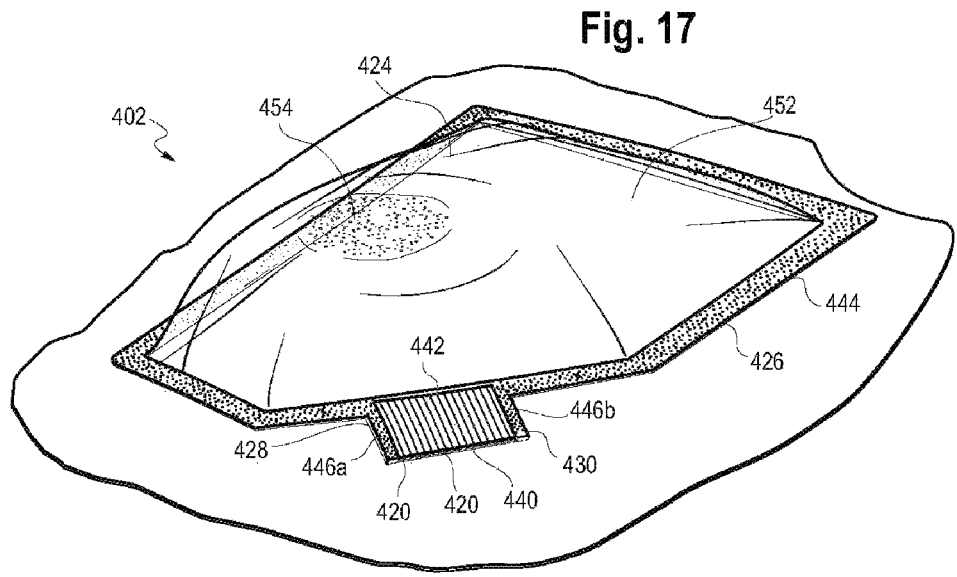
FIG. 17 is a perspective view of the flexible pouch of FIG. 16 in a tipped over state.

FIGS. 16-17 show an embodiment where the material for matrix 418 is an ethylene-based polymer with an M-surface tension of 31.6 dyn/cm. The liquid 454 is an aqueous based solution with an L-surface tension of 72 dyn/cm. When the opened flexible container 402 is accidentally tipped over (shown by downward arrow E in FIG. 16), resulting in the spilled flexible container 402 in FIG. 17, the non-wetting interface between the channels 420 and the aqueous solution (liquid 454) having a L-surface tension of 72 dyn/cm remains in the storage compartment 452 and does not leak, or otherwise drip, through the channels 420 at the exposed outer edge 440.

Figure 18:
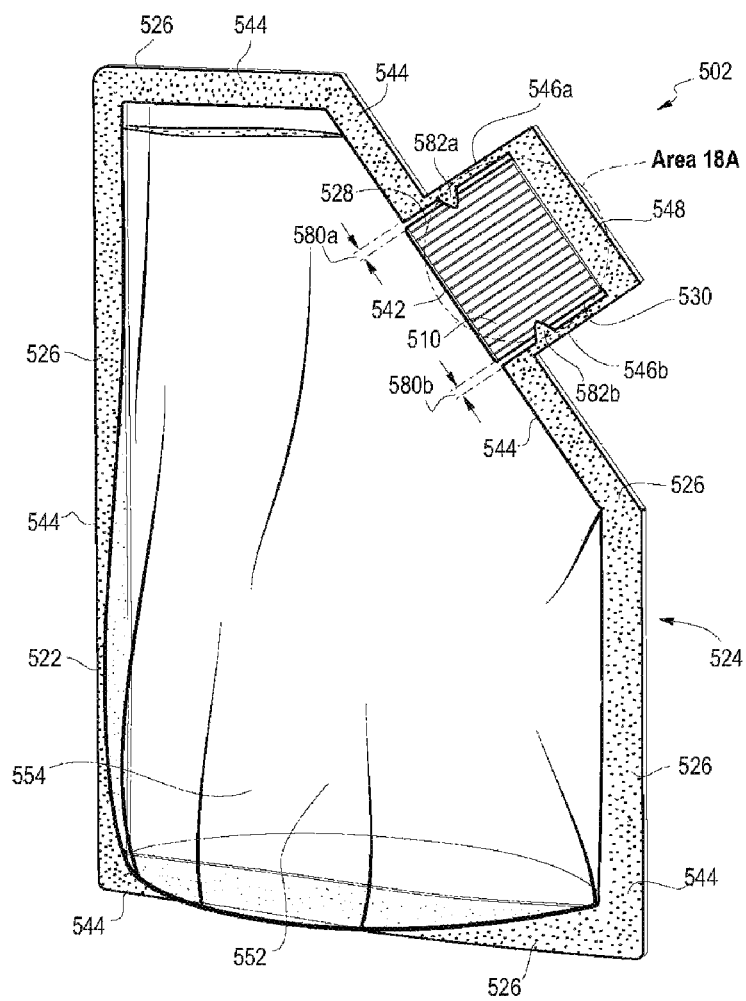
FIG. 18 is a perspective view of a flexible pouch in accordance with an embodiment of the present disclosure.
Figure 18A:
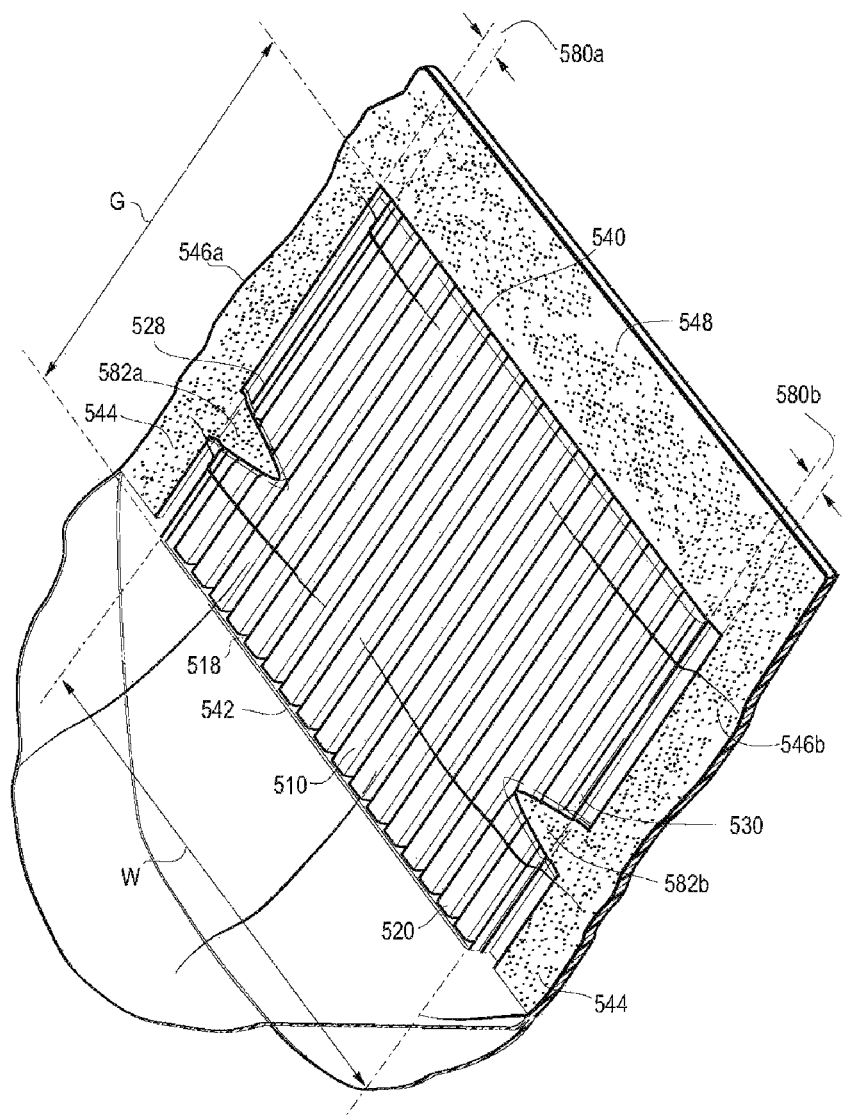
FIG. 18A is an enlarged perspective view of area 18A of FIG. 18.
Figure 19:
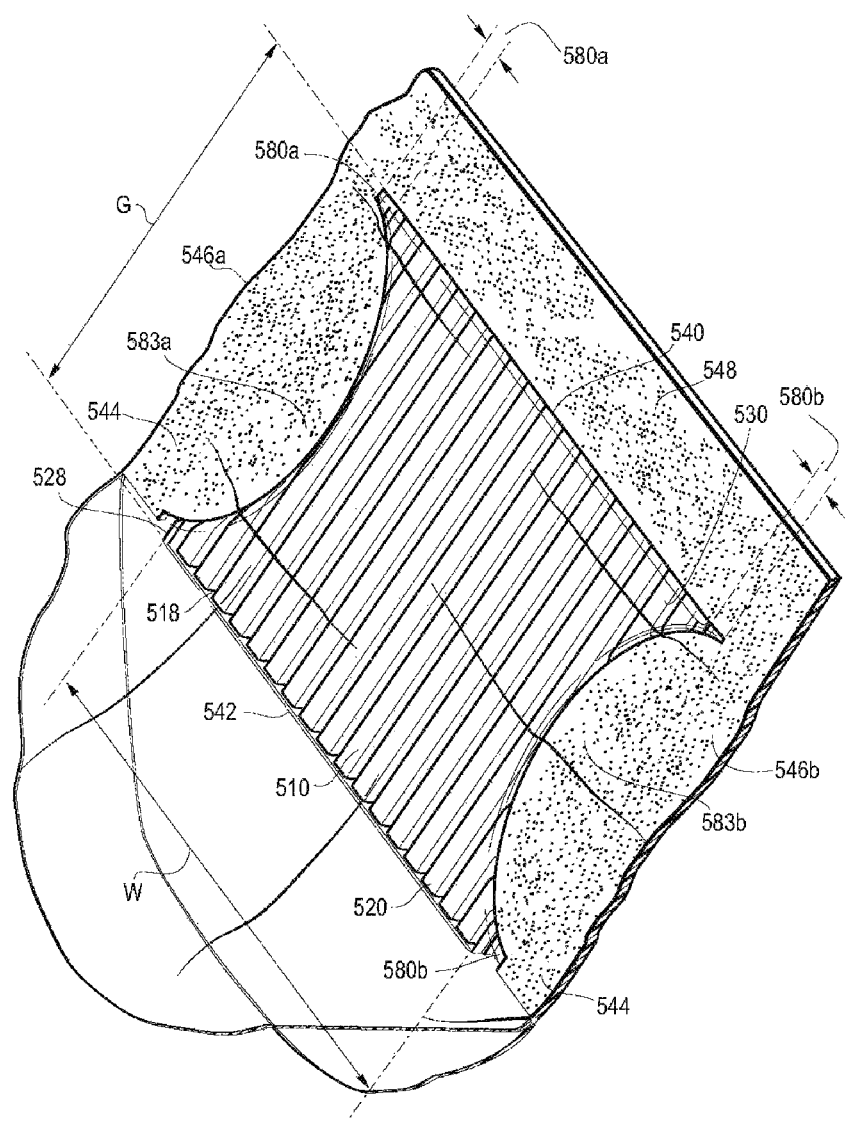
FIG. 19 is an enlarged perspective view of area 18A of FIG. 18 in accordance with another embodiment of the present disclosure.

FIGS. 18, 18A and 19 provide an embodiment, wherein the flexible pouch 502 includes a gap (580a, 580b) between a side seal (546a and/or 546b) and the respective side (528, 530) of the microcapillary strip 510, the side seal (546a and/or 546b) including a protrusion (582a, 582b of FIGS. 18 and 18A; 583a, 583b of FIG. 19) extending across the gap (580a, 580b). As used herein, a "gap" is an un-sealed area forming a void that is located between a side seal and a respective side of the microcapillary strip. A "protrusion" is a portion of the side seal and is a sealed area extending from a side seal across the gap. The protrusion, as part of the side seal, is formed by way of ultrasonic seal, heat seal, and combinations thereof. In an embodiment, the protrusion is a hermetic seal.

In FIG. 18, flexible pouch 502 includes microcapillary strip 510 sandwiched and sealed between opposing first flexible film 522 and second flexible film 524. The flexible films 522, 524 share a common peripheral edge 526. The microcapillary strip 510 has opposing sides, first side 528 and second side 530. The microcapillary strip 510 has opposing edges, outer edge 540 and inner edge 542.

The flexible pouch 502 has opposing gaps, first gap 580a and second gap 580b. The first gap 580a extends along a portion of (or along the entirely of) the first side 528 of the microcapillary strip 510. The second gap 580b extends along a portion of (or along the entirely of) the second side 530 of the microcapillary strip 510. In an embodiment, the gap (580a, 580b) extends from the inner edge 542 to the outer edge 540 of the microcapillary strip 510. While FIGS. 18, 18A and 19 depict flexible pouch 502 having two opposing gaps (580*a*, 580*b*), it is understood that the flexible pouch 502 may include a single (i.e., one and only one) gap (580*a* or 580*b*).

FIGS. 18 and 18A show a protrusion (582*a*, 582*b*) that extends across the gap (580*a*, 580*b*). In another embodiment, a protrusion (583*a*, 583*b*) extends across respective gaps 580*a*, 580*b*, as shown in FIG. 19. Each protrusion (582*a*, 582*b*, 583*a*, 583*b*) extends into at least one channel 520 of the microcapillary strip 510, thereby collapsing the at least one channel 520. In other words, the protrusion (582*a*, 582*b*, 583*a*, 583*b*) extends from a side seal (546*a* and/or 546*b*) across the gap (580*a*, 580*b*) and at least one channel 520, collapsing and forming a seal in the gap (580*a*, 580*b*) and the at least one channel 520. FIGS. 18 and 18A depict the flexible pouch 502 with a first protrusion 582*a* and a second protrusion 582*b*, each protrusion (582*a*, 582*b*) extending across a respective gap (580*a*, 580*b*). FIG. 19 depicts the flexible pouch 502 with a first protrusion 583*a* and a second protrusion 583*b*, each protrusion (583*a*, 583*b*) extending across a respective gap (580*a*, 580*b*). The protrusion defines a shape. Nonlimiting examples of suitable protrusion shapes include a polygon (such as triangle, square, rectangle, diamond, pentagon, hexagon, heptagon, octagon, etc.), or arcuate. FIGS. 18 and 18A depict a flexible pouch 502 with a first protrusion 582*a* and a second protrusion 582*b*, each protrusion (582*a*, 582*b*) having a triangle shape. FIG. 19 depicts a flexible pouch 502 with a first protrusion 583*a* and a second protrusion 583*b*, each protrusion (583*a*, 583*b*) having an arcuate shape. While FIGS. 18-19 depict flexible pouch 502 having two opposing protrusions (582*a*, 582*b* in FIGS. 18 and 18A, and 583*a*, 583*b* in FIG. 19), it is understood that the flexible pouch 502 may include a single (i.e., one and only one) protrusion when only a single gap exists between the microcapillary strip 510 and one side seal. Such a situation may occur when, during fabrication, one side of the microcapillary strip 510 abuts directly against a side seal (forming a hermetic seal) and the other side of the microcapillary strip 510 lies a distance away from its respective side seal, thereby creating a gap between the microcapillary strip side and the side seal.

In an embodiment, the protrusion (582*a*, 582*b*, 583*a*, 583*b*) extends across from 10%, or 15% to 20%, or 25%, or 30%, or 35%, or 40% of the width, W, of the microcapillary strip 510.

The protrusion (582*a*, 582*b*, 583*a*, 583*b*) extends across a portion of the gap (580*a*, 580*b*). In other words, the protrusion (582*a*, 582*b*, 583*a*, 583*b*) does not extend across the entire the gap (580*a*, 580*b*), such that the entire gap is sealed. In an embodiment, the protrusion (582*a*, 582*b*, 583*a*, 583*b*) extends across from 10%, or 15%, or 20%, or 25% to 30%, or 40%, or 50%, or 60%, or 70%, or 75%, or 80%, or 90%, or 95%, or 99% of the length, G, of the gap (580*a*, 580*b*), wherein the length, G, of the gap (580*a*, 580*b*) is equal to the distance between the outer edge 540 and the inner edge 542 of the microcapillary strip 510, as shown in FIGS. 18A and 19.

FIG. 18 shows a peripheral seal 544 that extends along a portion of (or along the entirety of) the common peripheral edge 526. The peripheral seal 544 includes side seals 546*a* and 546*b*. Side seal 546*a* extends along side 528 of the microcapillary strip 510. Side seal 546*b* extends along side 530 of the microcapillary strip 510.

The peripheral seal 544 also includes an edge seal 548. The edge seal 548 extends along the outer edge 540 of the microcapillary strip 510. As shown in FIGS. 18A and 19, the side seals 546*a*, 546*b* extend along respective gaps 580*a*, 580*b*. The edge seal 548 abuts against the outer edge 540 of the microcapillary strip 510. The edge seal 548 does not contact the protrusion (582*a*, 582*b*, 583*a*, 583*b*).

In an embodiment, the edge seal 548 is a release member that is a tear seal.

In an embodiment, the matrix 518 of microcapillary strip 510 is composed of a material having an (M-surface tension from 15 dyn/cm, or 17 dyn/cm, or 20 dyn/cm, or 22 dyn/cm, or 23 dyn/cm to 25 dyn/cm, or 27 dyn/cm, or 29 dyn/cm, or 30 dyn/cm, or 32 dyn/cm. The liquid 554 in the storage compartment has an L-surface tension) greater than or equal to 70 dyn/cm, or 71 dyn/cm, or 72 dyn/cm, or 75 dyn/cm, or 77 dyn/cm to 80 dyn/cm, or 85 dyn/cm, or 90 dyn/cm. Applicant discovered a flexible pouch with a microcapillary strip having a matrix material with an M-surface tension from 15 dyn/cm to 32 dyn/cm mated with a liquid having a an L-surface tension from greater than 70 dyn/cm to 90 dyn/cm yields a non-wetting surface interface between the stored liquid and the channels 520. The non-wetting interface holds the liquid within the storage chamber 552 and reduces leak when the open flexible container is spilled or tipped.

Nonlimiting examples of suitable materials for the matrix 518 with an M-surface tension from 15 dyn/cm to 32 dyn/cm are provided in Table 1. Nonlimiting examples of suitable liquids having an L-surface tension from greater than 70 dyn/cm to 90 dyn/cm are provided in Table 2. In an embodiment, the material for matrix 518 has an M-surface tension from 15 dyn/cm to 32 dyn/cm (as disclosed above) and is selected from an ethylene-based polymer, or a propylene-based polymer. The liquid 554 has an L-surface tension from greater than or equal to 70 dyn/cm to 85 dyn/cm, and the liquid is an aqueous-based solution.

In an embodiment, the material for matrix 518 of the microcapillary strip 510 is composed of a material having an M-surface tension from greater than 32 dyn/cm, or 35 dyn/cm, or 37 dyn/cm to 40 dyn/cm, or 43 dyn/cm, or 45 dyn/cm, or 47 dyn/cm, or 50 dyn/cm. The liquid 554 has an L-surface tension less than 70 dyn/cm, or from 15 dyn/cm, or 20 dyn/cm, or 25 dyn/cm, or 30 dyn/cm, or 35 dyn/cm, or 40 dyn/cm to 50 dyn/cm, or 55 dyn/cm, or 60 dyn/cm, or 65 dyn/cm, or 69 dyn/cm, or less than 70 dyn/cm. In a further embodiment, the liquid 554 having an L-surface tension from 15 dyn/cm to less than 70 dyn/cm is a non-aqueous liquid.

By way of example, and not limitation, examples of the present disclosure are provided.

EXAMPLES

1. Multilayer Film

TABLE 5

Composition of the Flexible Multilayer Film (Film 1) Laminated Multilayer Film

| Material | Description | Density (g/cm³) ASTM D792 | Melt Index (g/10 min) ASTM D1238 | Melting Point (° C.) DSC | Thickness (micrometer) |
|---|---|---|---|---|---|
| LLDPE | Dowlex ™ 2049 | 0.926 | 1 | 121 | 20 |
| HDPE | Elite ™ 5960G | 0.962 | 0.85 | 134 | 20 |
| LLDPE | Elite ™ 5400G | 0.916 | 1 | 123 | 19 |
| Adhesive Layer | Polyurethane solvent-less adhesive (ex., Morfree 970/CR137) | | | | 2 |
| HDPE | Elite ™ 5960G | 0.962 | 0.85 | 134 | 19 |
| HDPE | Elite ™ 5960G | 0.962 | 0.85 | 134 | 20 |
| Seal Layer | Affinity ™ 1146 | 0.899 | 1 | 95 | 20 |
| | Total | | | | 120 |

2. Flexible Stand-Up Pouch with Microcapillary Strip Made In Situ (Example 1)

A. Microcapillary 1

The channels (capillaries) are produced by using a parallel array of hardened stainless steel wires disposed between two monolayer sheets of INFUSE™ 9500 previously prepared by compression molding.

INFUSE™ 9500 strip dimensions: approximately 1 cm by 5 cm
Thickness (T): 0.22 mm
Stainless steel wire diameter (D): 0.22 mm
Wire spacing (S): 0.44 mm
Number of pins: 17

B. Microcapillary 2

The channels (capillaries) are produced by using a capillary precursor element (CPE) with an array of non-parallel (divergent) nickel titanium alloy wires disposed between two monolayer sheets of INFUSE™ 9107 (INFUSE strips) previously prepared by compression molding as disclosed in WO 2017/003865, published 5 Jan. 2017.

INFUSE™ 9107 strip dimensions: approximately 1 cm by 5 cm
Thickness (T): 300 micrometers
Stainless steel wire diameter (D): 400 micrometers
Wire spacing (S): 800 micrometers at the base
Number of pins: 13

C. Functionality Demonstration

The corner of the pouch is removed cut off using a regular scissors to remove sealed microcapillary segment, thereby exposing the edges of the channels. The pouch is gently squeezed by hand and a fine spray of an aqueous solution is discharged from the pouch as depicted in FIG. 5 (parallel channels) and FIG. 8A (non-parallel channels).

D. Leak Reduction 25 cm×18 cm flexible pouches (1250 ml volume) are made with opposing films of Film 1. The flexible pouches include side seals and an edge seal around the microcapillary strip and with the configuration shown in FIGS. 14-17. The pouches are prepared with varying materials for the microcapillary strip. The flexible pouches are filled with either water (L-surface tension 72 dyn/cm) or an aqueous soap solution (L-surface tension 25 dyn/cm). The composition of the soap solution is provided in Table 4.

Table 6 provides the composition and structure of four microcapillary strips.

TABLE 6

Material, composition, and properties for matrix materials

| Microcapillary Material | Commercial Name | Composition | I2 | Density | Surface tension (dyn/cm) | Film Thickness (mil) | Microcapillary Voidage (%) | Capillary size (microns) (G; H) |
|---|---|---|---|---|---|---|---|---|
| Material 1 | Elite 5100 | Ethylene-octene copolymer | 0.85 | 0.920 | 31.6 | 32.3 | 41.6 | 1078 × 480 |
| Material 2 | Amplify EA 100 | Ethylene-Ethyl Acrylate (15%) | 1.3 | — | 35 | 31.0 | 33.8 | 1053 × 382 |
| Material 3 | Amplify IO 3801 | Na based IO | 1.25 | — | 33 | 30 | 30.5 | 998 × 370 |
| Material 4 | Primacor 1410 | Ethylene-acrylic acid (9.7) | 1.45 | — | 35.1 | 31.4 | 32.8 | 1110 × 386 |

Eight flexible pouches are opened and inverted so the open and exposed edge of each microcapillary strip drains freely by way of gravity. The time between pouch inversion and evacuation of the liquid is measured. The pouch is deemed evacuated when continuous flow of the liquid through the channels ends and begins to drip through the channels. This is the "evacuation time," measured in seconds, and is recorded in Table 7 below.

TABLE 7

| Material for Matrix | Material 1 | Material 1 | Material 2 | Material 2 | Material 3 | Material 3 | Material 4 | Material 4 |
|---|---|---|---|---|---|---|---|---|
| Liquid | Water | Soap solution | Water | Soap solution | Water | Soap solution | Water | Soap solution |
| Capillary Length (mm) | 10 | 10 | 10 | 10 | 10 | 10 | 10 | 10 |
| Evacuation Time | 308 | 265 | 540 | 550 | 512 | 660 | 320 | 510 |

A longer evacuation time for a given matrix material indicates non-wettability between the liquid and the channels. Material 1 (M-surface tension 31.6 dyn/cm) retains water (L-surface tension 72 dyn/cm) better (longer evacuation time) than soap solution (L-surface tension 25 dyn/cm).

Materials 2, 3, 4 (respective M-surface tensions 35, 33, and 35.1 dyn/cm) retain soap solution (L-surface tension 25 dyn/cm) better than water 72 dyn/cm.

It is specifically intended that the present disclosure not be limited to the embodiments and illustrations contained herein, but include modified forms of those embodiments including portions of the embodiments and combinations of elements of different embodiments as come within the scope of the following claims.

We claim:

1. A flexible pouch comprising:
opposing flexible films, the flexible films defining a common peripheral edge;
a microcapillary strip sealed between the opposing flexible films;
a first side of the microcapillary strip located at a first side of the common peripheral edge and a second side of the microcapillary strip located at a second side of the common peripheral edge;
the first side of the common peripheral edge intersecting with the second side of the common peripheral edge to form a corner;
the microcapillary strip having an outer edge, and the outer edge forms an angle with the second side of the common peripheral edge at the corner;
a peripheral seal along at least a portion of the common peripheral edge, the peripheral seal comprising a sealed microcapillary segment, the peripheral seal forming a closed flexible pouch having a storage compartment; and
a liquid in the storage compartment.

2. The flexible pouch of claim 1 wherein the microcapillary strip is composed of a matrix material, the matrix material having a material surface tension (M-surface tension) from 15 dyn/cm to 32 dyn/cm as measured in accordance with ASTM D 2578; and
a liquid in the storage compartment, the liquid having a liquid surface tension (L-surface tension) greater than or equal to 70 dyn/cm as measured in accordance with ASTM D 2578.

3. The flexible pouch of claim 2 wherein the matrix material is selected from the group consisting of ethylene-based polymer and propylene-based polymer; and
the liquid is an aqueous-based solution.

4. The flexible pouch of claim 1 wherein the microcapillary strip is composed of a matrix material, the matrix material having a material surface tension (M-surface tension) from greater than 32 dyn/cm to 50 dyn/cm as measured in accordance with ASTM D 2578;
a liquid in the storage compartment, the liquid having a liquid surface tension (L-surface tension) less than 70 dyn/cm as measured in accordance with ASTM D 2578.

5. The flexible pouch of claim 4 wherein the liquid is a non-aqueous liquid.

6. A flexible pouch comprising:
opposing flexible films, the flexible films defining a common peripheral edge;
a microcapillary strip located at an edge offset distance between the opposing flexible films, the microcapillary strip sealed between the opposing flexible films;
a first side of the microcapillary strip located at a first side of the common peripheral edge and a second side of the microcapillary strip located at a second side of the common peripheral edge; and
a peripheral seal along at least a portion of the common peripheral edge, the peripheral edge comprising a sealed microcapillary segment, the peripheral seal forming a closed flexible pouch having a storage compartment and a pocket;
a liquid in the storage compartment;
wherein the microcapillary strip is composed of a matrix material,
(i) the matrix material has a material surface tension (M-surface tension) from 15 dyn/cm to 32 dyn/cm as measured in accordance with ASTM D 2578, and the liquid has a liquid surface tension (L-surface tension) greater than or equal to 70 dyn/cm as measured in accordance with ASTM D 2578; or
(ii) the matrix material has a material surface tension (M-surface tension) from greater than 32 dyn/cm to 50 dyn/cm as measured in accordance with ASTM D 2578, and the liquid has a liquid surface tension (L-surface tension) less than 70 dyn/cm as measured in accordance with ASTM D 2578.

7. The flexible pouch of claim 6 wherein the matrix material is selected from the group consisting of ethylene-based polymer and propylene-based polymer; and
the liquid is an aqueous-based solution.

8. A flexible pouch comprising:
opposing flexible films, the flexible films defining a common peripheral edge;
a microcapillary strip sealed between the opposing flexible films, the microcapillary strip comprising opposing sides and opposing edges;
a peripheral seal along at least a portion of the common peripheral edge, the peripheral seal comprising
(i) a side seal along each side of the microcapillary strip, and
(ii) an edge seal along an outer edge of the microcapillary strip;

(iii) the side seals and the edge seal abut the microcapillary strip and do not collapse the microcapillary strip; and the peripheral seal forms a closed flexible pouch having a storage compartment.

9. The flexible pouch of claim 8 wherein a gap is present between a side seal and the respective side of the microcapillary strip, and the side seal comprises a protrusion extending across the gap.

10. The flexible pouch of claim 8 wherein the microcapillary strip is composed of a matrix material, the matrix material having a material surface tension (M-surface tension) from 15 dyn/cm to 32 dyn/cm as measured in accordance with ASTM D 2578;

a liquid in the storage compartment, the liquid having a liquid surface tension (L-surface tension) greater than or equal to 70 dyn/cm as measured in accordance with ASTM D 2578.

11. The flexible pouch of claim 10 wherein the matrix material is selected from the group consisting of ethylene-based polymer and propylene-based polymer; and the liquid is an aqueous-based solution.

12. The flexible pouch of claim 8 wherein the microcapillary strip is composed of a matrix material, the matrix material having a material surface tension (M-surface tension) from greater than 32 dyn/cm to 50 dyn/cm as measured in accordance with ASTM D 2578;

a liquid in the storage compartment, the liquid having a liquid surface tension (L-surface tension) less than 70 dyn/cm as measured in accordance with ASTM D 2578.

* * * * *